(12) United States Patent
Motterlini et al.

(10) Patent No.: US 7,989,650 B2
(45) Date of Patent: *Aug. 2, 2011

(54) THERAPEUTIC DELIVERY OF CARBON MONOXIDE TO EXTRACORPOREAL AND ISOLATED ORGANS

(75) Inventors: Roberto Angelo Motterlini, Middlesex (GB); Brian Ernest Mann, Sheffield (GB)

(73) Assignee: hemoCORM Limited, London (GB)

( * ) Notice: Subject to any disclaimer, the term of this patent is extended or adjusted under 35 U.S.C. 154(b) by 357 days.

This patent is subject to a terminal disclaimer.

(21) Appl. No.: 10/535,508

(22) PCT Filed: Nov. 20, 2003

(86) PCT No.: PCT/GB03/05050
§ 371 (c)(1),
(2), (4) Date: Dec. 16, 2005

(87) PCT Pub. No.: WO2004/045598
PCT Pub. Date: Jun. 3, 2004

(65) Prior Publication Data
US 2006/0127501 A1    Jun. 15, 2006

(30) Foreign Application Priority Data
Nov. 20, 2002  (GB) .................................. 0227138.5

(51) Int. Cl.
*C07F 17/00* (2006.01)
(52) U.S. Cl. ............. 556/46; 514/492; 514/502; 556/45
(58) Field of Classification Search .................. 514/492, 514/502; 556/45, 46
See application file for complete search history.

(56) References Cited

U.S. PATENT DOCUMENTS

| | | |
|---|---|---|
| 2,870,180 A | 1/1959 | Kozikowski et al. |
| 3,278,570 A | 10/1966 | Wilkinson et al. |
| 3,694,232 A | 9/1972 | Hall et al. |
| 3,812,166 A | 5/1974 | Wiechert |
| 3,829,504 A | 8/1974 | Hall et al. |
| 3,980,583 A | 9/1976 | Mitchell et al. |
| 4,189,487 A | 2/1980 | Klosa |
| 4,312,989 A | 1/1982 | Spielvogel et al. |
| 4,322,411 A | 3/1982 | Vinegar et al. |
| 4,613,621 A | 9/1986 | Horrmann |
| 4,649,151 A | 3/1987 | Dougherty et al. |
| 4,657,902 A | 4/1987 | Kappas et al. |
| 4,668,670 A | 5/1987 | Rideout et al. |
| 4,699,903 A | 10/1987 | Rideout et al. |
| 4,709,083 A | 11/1987 | Spielvogel |
| 4,910,211 A | 3/1990 | Imamura et al. |
| 4,938,949 A | 7/1990 | Borch et al. |
| 5,010,073 A | 4/1991 | Kappas et al. |
| 5,086,060 A | 2/1992 | Haley et al. |
| 5,102,670 A | 4/1992 | Abraham et al. |
| 5,254,706 A | 10/1993 | Spielvogel et al. |
| 5,312,816 A | 5/1994 | Spielvogel et al. |
| 5,350,767 A | 9/1994 | Hallberg et al. |
| 5,447,939 A | 9/1995 | Glasky et al. |
| 5,621,000 A | 4/1997 | Arena et al. |
| 5,631,284 A | 5/1997 | Legzdins et al. |
| 5,659,027 A | 8/1997 | Spielvogel et al. |
| 5,664,563 A | 9/1997 | Schroeder et al. |
| 5,670,664 A | 9/1997 | Kao et al. |
| 5,700,947 A | 12/1997 | Soldato |
| 5,756,492 A | 5/1998 | Buelow et al. |
| 5,767,157 A | 6/1998 | Van Moerkerken |
| 5,801,184 A | 9/1998 | Glasky et al. |
| 5,811,463 A | 9/1998 | Legzdins et al. |
| 5,824,673 A | 10/1998 | Abrams et al. |
| 5,861,426 A | 1/1999 | Del Soldato et al. |
| 5,882,674 A | 3/1999 | List et al. |
| 5,885,621 A | 3/1999 | Head et al. |
| 5,888,982 A | 3/1999 | Perrella et al. |
| 5,891,689 A | 4/1999 | Takle et al. |
| 6,025,394 A | 2/2000 | Menander et al. |
| 6,027,936 A | 2/2000 | Glasky |
| 6,040,341 A | 3/2000 | Del Soldato et al. |
| 6,051,576 A | 4/2000 | Ashton et al. |
| 6,060,467 A | 5/2000 | Buelow et al. |
| 6,066,333 A | 5/2000 | Willis et al. |
| 6,177,471 B1 | 1/2001 | Menander et al. |
| 6,203,991 B1 | 3/2001 | Nabel et al. |

(Continued)

FOREIGN PATENT DOCUMENTS

DE        4014762 A1    11/1991
(Continued)

OTHER PUBLICATIONS

Motterlini et al., Carbon Monoxide-Releasing Molecules Characterization of Biochemical and Vascular Activities, Feb. 8, 2002, Circulation Research, vol. 90, pp. 17-24. (See IDS).*

(Continued)

*Primary Examiner* — Karlheinz R Skowronek
*Assistant Examiner* — Ali Soroush
(74) *Attorney, Agent, or Firm* — Wolf, Greenfield & Sacks, P.C.

(57) ABSTRACT

Metal carbonyls are used to deliver CO to organs to limit post-ischaemic damage. The organ may be extracorporeal, e.g. for use in a transplant, or may be an isolated organ inside or attached to the body but isolated from the blood flow. The carbonyl preferably has one or more other ligands other than CO, such as amino acids, to modulate the CO release property and solubility.

13 Claims, 10 Drawing Sheets

U.S. PATENT DOCUMENTS

| | | | |
|---|---|---|---|
| 6,211,233 B1 | 4/2001 | Del Soldato | |
| 6,218,417 B1 | 4/2001 | Del Soldato | |
| 6,242,432 B1 | 6/2001 | del Soldato | |
| 6,251,927 B1 | 6/2001 | Lai et al. | |
| 6,284,752 B1 | 9/2001 | Abrams et al. | |
| 6,331,564 B1 | 12/2001 | Brugnara et al. | |
| 6,338,963 B1 | 1/2002 | Glasky et al. | |
| 6,344,178 B1 | 2/2002 | Alberto et al. | |
| 6,350,752 B1 | 2/2002 | Glasky et al. | |
| 6,417,182 B1 | 7/2002 | Abrams et al. | |
| 6,518,269 B1 | 2/2003 | Camden et al. | |
| 6,645,938 B2 * | 11/2003 | Oeltgen et al. | 514/13 |
| 6,673,908 B1 | 1/2004 | Stanton, Jr. | |
| 7,011,854 B2 * | 3/2006 | Haas et al. | 424/699 |
| 7,045,140 B2 | 5/2006 | Motterlini | |
| 7,053,242 B1 | 5/2006 | Alberto et al. | |
| 2002/0045611 A1 | 4/2002 | Abrams et al. | |
| 2002/0155166 A1 | 10/2002 | Choi et al. | |
| 2002/0165242 A1 | 11/2002 | Glasky et al. | |
| 2002/0193363 A1 | 12/2002 | Bridger et al. | |
| 2003/0039638 A1 | 2/2003 | Bach et al. | |
| 2003/0064114 A1 | 4/2003 | Motterlini et al. | |
| 2003/0068387 A1 | 4/2003 | Buelow et al. | |
| 2003/0124157 A1 | 7/2003 | Engles et al. | |
| 2003/0157154 A1 | 8/2003 | Fuller et al. | |
| 2003/0207786 A1 | 11/2003 | Miracle et al. | |
| 2003/0219496 A1 | 11/2003 | Otterbein et al. | |
| 2003/0219497 A1 | 11/2003 | Otterbein et al. | |
| 2004/0052866 A1 | 3/2004 | Otterbein et al. | |
| 2004/0067261 A1 | 4/2004 | Haas et al. | |
| 2004/0122091 A1 | 6/2004 | Dasseux et al. | |
| 2004/0131602 A1 | 7/2004 | Buelow et al. | |
| 2004/0143025 A1 | 7/2004 | Buelow et al. | |
| 2004/0214900 A1 | 10/2004 | Forbes et al. | |
| 2004/0228930 A1 | 11/2004 | Billiar et al. | |
| 2004/0258772 A1 | 12/2004 | Otterbein et al. | |
| 2005/0048133 A1 | 3/2005 | Pinsky et al. | |
| 2005/0175555 A1 | 8/2005 | Stradi et al. | |
| 2006/0115542 A1 | 6/2006 | Motterlini | |
| 2006/0147548 A1 | 7/2006 | Motterlini | |
| 2006/0148900 A1 | 7/2006 | Haas et al. | |
| 2006/0233890 A1 | 10/2006 | Haas et al. | |
| 2007/0065485 A1 | 3/2007 | Motterlini | |
| 2007/0207217 A1 | 9/2007 | Haas et al. | |
| 2007/0207993 A1 | 9/2007 | Haas et al. | |
| 2007/0219120 A1 | 9/2007 | De Matos et al. | |
| 2008/0026984 A1 | 1/2008 | De Matos et al. | |
| 2010/0105770 A1 | 4/2010 | Motterlini et al. | |

FOREIGN PATENT DOCUMENTS

| | | |
|---|---|---|
| EP | 0076493 A2 | 4/1983 |
| FR | 2816212 A1 | 5/2002 |
| GB | 1107510 A | 3/1968 |
| GB | 0111872.8 A | 7/1968 |
| GB | 0227135.1 A | 4/1994 |
| GB | 0227138.5 A | 4/1994 |
| GB | 2395431 A | 5/2004 |
| GB | 2395432 A | 5/2004 |
| HU | 57595 A2 | 12/1991 |
| HU | B-211 084 | 10/1995 |
| WO | WO-85/04326 A1 | 10/1985 |
| WO | WO 91/01128 | 2/1991 |
| WO | WO 91/01301 | 2/1991 |
| WO | WO-92/03402 A1 | 3/1992 |
| WO | WO-92/04905 A1 | 4/1992 |
| WO | 94/22482 A | 10/1994 |
| WO | WO 94/22482 | 10/1994 |
| WO | WO 95/05814 | 3/1995 |
| WO | WO-95/09831 | 4/1995 |
| WO | WO-95/35105 A1 | 12/1995 |
| WO | WO-96/03125 | 2/1996 |
| WO | WO-96/09038 | 3/1996 |
| WO | WO-97/16405 A1 | 5/1997 |
| WO | WO-97/36615 A1 | 10/1997 |
| WO | WO-97/37644 A1 | 10/1997 |
| WO | WO-98/09618 A2 | 3/1998 |
| WO | WO 98/29115 | 7/1998 |
| WO | WO-98/38179 A1 | 9/1998 |
| WO | WO-98/48848 | * 11/1998 |
| WO | WO 98/48848 | 11/1998 |
| WO | WO-99/67231 A1 | 12/1999 |
| WO | WO-00/10613 A2 | 3/2000 |
| WO | WO-00/21965 A1 | 4/2000 |
| WO | WO-00/36113 A2 | 6/2000 |
| WO | WO 00/56145 | 9/2000 |
| WO | WO 00/56743 | 9/2000 |
| WO | WO-00/61537 A2 | 10/2000 |
| WO | WO-01/12584 A2 | 2/2001 |
| WO | WO-01/16359 A2 | 3/2001 |
| WO | WO-01/28545 A2 | 4/2001 |
| WO | WO 02/078684 | 10/2002 |
| WO | WO 02/080923 | 10/2002 |
| WO | 02/092075 A | 11/2002 |
| WO | WO-02/092072 A2 | 11/2002 |
| WO | WO 02/092075 | 11/2002 |
| WO | WO 03/000114 | 1/2003 |
| WO | WO 03/066067 | 8/2003 |
| WO | WO-03/067598 A2 | 8/2003 |
| WO | WO 03/072024 | 9/2003 |
| WO | WO-03/082850 A1 | 10/2003 |
| WO | WO 03/088923 | 10/2003 |
| WO | WO 03/088981 | 10/2003 |
| WO | WO 03/094932 | 11/2003 |
| WO | WO-03/096977 A2 | 11/2003 |
| WO | WO-03/103585 A2 | 12/2003 |
| WO | WO-2004/029033 A1 | 4/2004 |
| WO | WO-2004/043341 A2 | 5/2004 |
| WO | WO-2004/045598 A1 | 6/2004 |
| WO | WO-2004/045599 A1 | 6/2004 |
| WO | WO-2004/080420 A2 | 9/2004 |
| WO | WO-2005/013691 A1 | 2/2005 |
| WO | WO-2005/090400 A1 | 9/2005 |
| WO | WO-2006/012215 A1 | 2/2006 |
| WO | WO-2007/073226 A1 | 6/2007 |
| WO | WO-2007/085806 A2 | 8/2007 |
| WO | WO-2008/003953 A2 | 1/2008 |
| WO | WO-2008/069688 A2 | 6/2008 |
| WO | WO-2008/130261 A1 | 10/2008 |
| WO | WO-2009/013612 A1 | 1/2009 |

OTHER PUBLICATIONS

Clark et al., Cardioprotective Actions by a Water-Soluble Carbon Monoxide-Releasing Molecule, Jul. 25, 2003, Circulation Research, vol. 93, pp. 2-8.*

R. Motterlini et al., "Carbon Monoxide-Releasing Molecules Characterization of Biochemical and Vascular Activities", Circulation Research, Grune and Stratton, vol. 90, No. 2, Feb. 8, 2002, pp. E17-E24, XP001159178.

Sjostrand T. Endogenous formation of carbon monoxide in man under normal and pathological conditions. Scan J Clin Lab Invest 1949;1:201-14.

Coburn RF, Blakemore WS, Forster RE, Endogenous carbon monoxide production in man. J Clin Invest 1963;42:1172-8.

Tenhunen R, Marver HS, Schmid R. Microsomal heme oxygenase. Characterization of the enzyme. J Biol Chem 1969;244:6388-94.

Maines MD. Heme oxygenase: function, multiplicity, regulatory mechanisms, and clinical applications. FASEB J 1988;2:2557-68.

Furchgott RF, Jothianandan D. Endothelium-dependent and -independent vasodilation involving cGMP: relaxation induced by nitric oxide, carbon monoxide and light. Blood Vessels 1991;28:52-61.

Morita T, Perrella MA, Lee ME, Kourembanas S. Smooth muscle cell-derived carbon monoxide is a regulator of vascular cGMP. Proc Natl Acad Sci USA 1995;92:1475-9.

Sammut IA, Foresti R, Clark JE, Exon DJ, Vesely MJJ, Sarathchandra P, Green CJ, Motterlini R. Carbon monoxide is a major contributor to the regulation of vascular tone in aortas expressing high levels of haeme oxygenase-1. Br J Pharmacol 1998;125:1437-44.

Maines MD. The heme oxygenase system: a regulator of second messenger gases. Annu Rev Pharmacol Toxicol 1997;37:517-54.

Soares MP, Lin Y, Anrather J, Csizmadia E, Takigami K, Sato K, Grey ST, Colvin RP, Choi AM, Poss KD, et al. Expression of heme oxygenase-1 can determine cardiac xenograft survival. Nature Med 1998;4:1073-7.

Willis D, Moore AE, Frederick R, Willoughby DA. Heme oxygenase: a novel target for the modulation of inflammatory response. Nature Med 1996;2:87-90.

Motterlini R, Gonzales A, Foresti R, Clark JE, Green CJ, Winslow RM. Heme oxygenase-1-derived carbon monoxide contributes to the suppression of acute hypertensive responses in vivo. Circ Res 1998;83:568-77.

Otterbein LE, Mantell LL, Choi AMK. Carbon monoxide provides protection against hyperoxic lung injury. Am J Physiol 1999;276:L688-94.

Otterbein LE, Kolls JK, Mantell LL, Cook JL, Alam J, Choi Amk. Exogenous administration of heme oxygenase-1 by gene transfer provides protection against hyperoxia-induced lung injury. J Clin Invest 1999;103:1047-54.

Herrick RS, Brown TL. Flash photolytic investigation of photoinduced carbon monoxide dissociation from dinuclear manganese carbonyl compounds. lnorg Chem 1984;23:4550-3.

Alessio E, Milani B, Bolle M, Mestroni G, Falechini P, Todone F, Geremia S, Calligaris M. Carbonyl derivatives of chloride-dimethyl sulfoxide-ruthenium(II) complexes: synthesis, structural characterization, and reactivity of Ru(CO)x(DMSO)4-xCI2 complexes (x=1-3). lnorg Chem 1995;34:4722-34.

Sato K., Balla J., Otterbein L., Smith R.N., Brouard S., Lin Y., Csizmadia E., Sevigny J., Robson S.C., Vercellotti G., Choi A.M., Bach F.H., Soares M.P. Carbon monoxide generated by heme oxygenase-1 suppresses the rejection of mouse-to-rat cardiac transplants. *J.Immunol.* 166:4185-4194, 2001.

G. Pneumatikakis, A. Yannopoulos and J. Markopoulos, *Inorg. Chim. Acta*, 1988, 151, 243.

Motterlini R. et al., Carbon monoxide-releasing molecules: characterization of biomedical and vascular Circulation Research. 2002, vol. 90, No. 2, E17-E24.

Yan Y.K. et al., Cytotoxicity of rhenium (I) alkoxo and hydroxo carbonyl complexes in murin and human tumor cells, Pharmazie (2000), 55(4), 307-313.

Becker M.J. et al., Age related changes in antibody dependent cell mediatedcytotoxicity in mouse spleen, Israel J. Medical Sciences (1979), vol. 15, No. 2, 147-150.

Nagai M. et al., Unusual CO bonding geometry in abnormal subunits of hemoglobin M Boston and hemoglobin M Saskatoon, Biochemistry (1991), vol. 30, No. 26, 6495-6503.

Tomita A. et al., Structure and reaction of bis(L-cysteinato)dicarbonyliron(II), Inorganic and Nuclear Chemistry Letters (1968), 4(12), 715-18.

Ferrier, F.; Terzian, G.; Mossoyan, J.; Benlian, D, FTIR spectrometric study of geometrical isomers of dicarbonyl ferrobiscysteinate Influence of the counter cation. Laboratoire de Chimie de Coordination, D22, Universite de Provence, Av. Escadrille Normandie-Niemen, Marseille, Fr. J. Mol. Struct. (1995), 344(3), 189-93. CODEN: JMOSB4 ISSN: 0022-2860. Journal written in English. CAN 122:250765 AN 1995:414110 CAPLUS (Copyright 2002 ACS).

Szakacs-Schmidt, Aniko; Kreisz, Jozsef; Marko, Laszlo; Nagy-Magos, Zsuzsa; Takacs, Janos, Iron(II) thiolates as reversible carbon monoxide carriers, Res. Inst. Chem. Eng., Hung. Acad. Sci., Veszprem, Hung. Inorg. Chim. Acta (1992), 198-200 401-5. CODEN: ICHAA3 ISSN: 0020-1693. Journal written in English. CAN 117:263637 AN 1992:663637 CAPLUS (Copyright 2002 ACS).

Takacs, Janos; Soos, Erika; Nagy-Magos, Zsuzsa; Marko, Laszlo; Gervasio, Giuliana; Hoffmann, Thomas, Synthesis and molecular structure of carbonyl derivatives of iron(II) thiolates containing nitrogen-donor ligands, Res. Group Petrochem., Hung. Acad. Sci., Veszprem, Hung. Inorg. Chim. Acta (1989), 166(1), 39-46. CODEN: ICHAA3 ISSN: 0020-1693. Journal written in English. CAN 113:16859 AN 1990:416859 CAPLUS (Copyright 2002 ACS).

Carroll, James A.; Fisher, David R.; Rayner-Canham, Geoffrey W.; Sutton, Derek, Ligand abstraction in the reaction of aryldiazonium ions with some iron complexes containing coordinated cysteine, maleonitriledithiol, or triarylphosphine, Dep. Chem., Simon Fraser Univ., Burnaby, B. C., Can. Can. J. Chem. (1974), 52(10), 1914-22. CODEN: CJCHAG Journal written in English. CAN 81:32728 AN 1974:432728 CAPLUS (Copyright 2002 ACS).

M.P. Schubert, The action of carbon monoxide on iron and cobalt complexes of cysteine, J. Am. Chem. Soc., 1933, 55, 4564-4570.D54.

Y. Huang, M.C. Marden, J.C. Lambry, M.P., Photolysis of the histidine-heme-carbon monoxide copmplex, Fontaine-Aupart, R. Pansu, J.L. Martin and C. Poyart, J. Am. Chem. Soc., 1991, 113, 9141.

J. Silver and B. Lukas, Moessbauer studies oh protoporphyrin IX iron (II) solutions containing sulfur ligands and their carbonyl adducts. Models for the active site of cytochromes P.450, Inorg. Chim. Acta, 1984, 91, 279.

C.M. Wang and W.S., A correlation of the visible and Soret spectra of dioxygen- and carbon monoxide-heme complexes and five-coordinate heme complexes with the spectra of oxy-, carboxy-, and deoxyhemoglobons, Brinigar, Biochemistry, 1979, 18, 4960.

A.A. Diamentis and J.V. Dubrawski, Preparation and structure of ethylenediaminetetraacetate complexes and other $\pi$-acceptor ligands, Inorganic Chemistry (1981), 20(4), 1142-1150.

R. Urban et. al., Metal complexes of biologically important ligands, LXXXVII alpha-amino carboxylate complexes of palladium(II), iridium(III) and ruthenium(II) from chloro-bridged ortho-metallated metal compounds and [(OC)3Ru(CI)(µ-CL)]2, Organomet. Chem. 1996, 517 191.

Nydegger, U. E. et al.; "New concepts in organ preservation"; Transplant Immunology; 2002; 9; 215-25.

Holmuhamedov, E. L. et al.; "Mitochondrial ATP-sensitive K+ channels modulate cardiac mitochondrial function."; Am. J. Physiol.; 1998; 275; H1567-76.

Lawton, J. S. et al.; "Myocardial oxygen consumption in the rabbit heart after ischemia: hyperpolarized arrest with pinacidil versus depolarized hyperkalemic arrest."; Circulation; 1997; 96(9 Suppl): II-247-52.

Motterlini R. et al.; "Carbon monoxide-releasing molecules: characterization of biochemical and vascular activities"; Circ. Res.; 2002; 90; E17-E24.

Motterlini, R. et al.; "Functional and metabolic effects of proprionyl-L-camitine in the isolated perfused hypertrophied rat heart"; Mol. Cell Biochem.; 1992; 116; 139-45.

Wang, L et al.; "Preconditioning limits mitochondrial $Ca^{2+}$ during ischemia in rat hearts: role of $K_{ATP}$ (channels)"; Am. J. Physiol. Heart Circ. Physiol.; 2001; 280; H2321-H2328.

Wang, R. et al.; "The chemical modification of $K_{ca}$ channels by carbon monoxide in vascular smooth muscle cells."; J. Biol. Chem.; 1997; 272; 8222-26.

Wu, L. et al.; "Different mechanisms underlying the stimulation of K(Ca) channels by nitric oxide and carbon monoxide."; J. Clin. Invest.; 2002; 110; 691-700.

Yachie, a. et al.; "Oxidative stress causes enhanced endothelial cell injury in human heme oxygenase-1 deficiency"; J. Clin. Invest.; 1999; 103; 129-35.

Sacks, P. V. et al.; "Comparative bioavailability of elemental iron powders for repair of iron deficiency anemia in rats. Studies of efficacy and toxicity of carbonyl iron"; the American Journal of Clinical Nutrition; 1978; 31;566-73.

Huebers, H. A. et al.; "Absorption of carbonyl iron"; J. Lab. Clin. Med.; 1986; 108; 473-8.

Gordeuk, V. P. et al; "Carbonyl Iron Therapy for Iron Deficiency Anemia"; Blood; 1986; 67(3); 745-752.

Durante W.; "Heme Oxygenase-1 in Growth Control and its Clinical Application to Vascular Disease"; J. Cell. Physiol.; 2003; 195; 373-82.

Motterlini, R. et al.; "Characterization of vasoactive effects elicited by carbon monoxide-releasing molecules."; Journal of Vascular Research, Abstracts, 8th International Symposium on Mechanisms of Vasodilation; May 31-Jun. 3, 2001; 055.

Pending claims of U.S. Appl. No. 11/275,780 obtained from PTO IFW on Mar. 24, 2008.

Pending claims of U.S. Appl. No. 10/535,226 obtained from PTO IFW on Mar. 24, 2008.

Pending claims of U.S. Appl. No. 10/567,157 obtained from PTO IFW on Mar. 24, 2008.

Kamimura et al., The protective effect of carbon monoxide on the ischemia-induced cell death. The J Biochem. Aug. 2002;74(8):926. Japanese abstract.

Tamaki, Role of second messenger gases in ischemia and reperfusion injury. Low Temp Med. 2001;27(1):1-5.

Tsuburai et al., The role of heme oxygenase in pulmonary circulation. Low Temp Med. 2001;27(1):25-35.

Vulapalli et al., Cardioselective overexpression of HO-1 prevents I/R-induced cardiac dysfunction and apoptosis. Am J Physiol Heart Circ Physiol. Aug. 2002;283(2):H688-94.

Yet et al., Cardiac-specific expression of heme oxygenase-1 protects against ischemia and reperfusion injury in transgenic mice. Circ Res. Jul. 20, 2001;89(2):168-73.

[No Author Listed] "supramolecule" IUPAC compendium of chemical terminology. Retrieved from the internet at www.iupac.org/goldbook/SO6153.pdf on May 8, 2006.

[No Author Listed] Biosis Chem Abstracts Database. Accession No. PREV200600414130.2005. Otterbein et al., Cell Mol Biol (Noisy-le-grand). Oct. 3, 2005;51(5):433-40. Abstract.

[No Author Listed] Chemical Abstracts. 2002;137:119662. (FR2816212).

[No Author Listed] Chemical Abstracts. 2004;140:40075. (WO2004/043341).

[No Author Listed] Chemical Abstracts. 2004;141:270758. (Ryter et al.).

[No Author Listed] Chemical Abstracts. 2004;142:211995. (Stein et al.).

Abel et al., Anionic halogenopentacarbonyls of chromium, molybdenum, and tungsten. J Chem Soc. 1963:2068-70.

Abel et al., Carbonyl halides of manganese and some related compounds. J Chem Soc. 1959;Part 2:1501-5.

Abel et al., Reaction of molybdenum carbonyl with various halides: a potassium etherate salt. Chem Indust. 1960;442.

Abraham et al., The biological significance and physiological role of heme oxygenase. Cell Physiol Biochem. 1996;6:129-68.

Adkison et al., Semicarbazone-based inhibitors of cathepsin K, are they prodrugs for aldehyde inhibitors? Bioorg Med Chem Lett. Feb. 15, 2006;16(4):978-83. Epub Nov. 15, 2005. Abstract only.

Akamatsu et al., Heme oxygenase-1-derived carbon monoxide protects hearts from transplant associated ischemia reperfusion injury. FASEB J. Apr. 2004;18(6):771-2. Epub Feb. 20, 2004.

Alberto et al., A novel organometallic aqua complex of technetium for the labeling of biomolecules: synthesis of [99mTc(OH2)3(CO)3]+ from [99mTcO4]- in aqueous solution and its reaction with a bifunctional ligand. J Am Chem Soc. 1998;120:7987-8.

Alberto et al., Synthesis and properties of boranocarbonate: a convenient in situ CO source for the aqueous preparation of [(99m)Tc(OH(2))3(Co)3]+. J Am Chem Soc. Apr. 4, 2001;123(13):3135-6.

Alessio et al., Carbonyl Derivatives of Chloride-Dimethyl Sulfoxide-Ruthenium(III) Complexes: Synthesis, Crystal Structure, and Reactivity of [(DMSO)2H][trans-RuCl4(DMSO-O)(CO)] and mer,cis-RuCl3(DMSO-O)2(CO). Inorg Chem. 1995;34(19):4716-21.

Allanson et al., Ultraviolet a (320-400 nm) modulation of ultraviolet B (290-320 nm)-induced immune suppression is mediated by carbon monoxide. J Invest Dermatol. Mar. 2005;124(3):644-50.

Allardyce et al., Development of organometallic (organo-transition metal) pharmaceuticals. Appl Organomet Chem. 2005;19:1-10.

Amersi et al., Ex vivo exposure to carbon monoxide prevents hepatic ischemia/reperfusion injury through p38 MAP kinase pathway. Hepatology. Apr. 2002;35(4):815-23.

Andreadis et al., Oxidative and nitrosative events in asthma. Free Radic Biol Med. Aug. 1, 2003;35(3):213-25. Review. Abstract only.

Angelici et al., Carboxamido carbonyl complexes of manganese(I). Inorg Chim Acta. Mar. 1968;2:3-7. Abstract only.

Angelici, Preparation, characterization, and reactions of the cis-Dihalotetracarbonylmanganate(I) anions. Inorg Chem. Aug. 1964;3(8):1099-1102.

Aujard et al., Tridemethylisovelleral, a potent cytotoxic agent. Bioorg Med Chem. Nov. 15, 2005;13(22):6145-50. Epub Aug. 1, 2005. Abstract only.

Bagul et al., Carbon monoxide protects against ischemia-reperfusion injury in an experimental model of controlled nonheartbeating donor kidney. Transplantation. Feb. 27, 2008;85(4):576-81.

Bani-Hani et al., Modulation of thrombin-induced neuroinflammation in BV-2 microglia by carbon monoxide-releasing molecule 3. J Pharmacol Exp Ther. Sep. 2006;318(3):1315-22. Epub Jun. 13, 2006.

Bannenberg et al., Therapeutic applications of the gaseous mediators carbon monoxide and hydrogen sulfide. Expert Opin Ther Pat. May 2009;19(5):663-82. Review.

Barkoudah et al., The permissive role of endothelial NO In CO-induced cerebrovascular dilation. Am J Physiol Heart Circ Physiol. Oct. 2004;287(4):H1459-65. Epub Jun. 10, 2004.

Bauer et al., Evidence for a functional link between stress response and vascular control in hepatic portal circulation. Am J Physiol. Nov. 1996;271(5 Pt 1):G929-35.

Bauerová et al., Role of reactive oxygen and nitrogen species in etiopathogenesis of rheumatoid arthritis. Gen Physiol Biophys. Oct. 1999;18 Spec No:15-20. Review. Abstract only.

Beal, Oxidatively modified proteins in aging and disease. Free Radic Biol Med. May 1, 2002;32(9):797-803. Review. Abstract only.

Beaty et al., An in vitro model for the in vivo mobilization of cadmium by chelating agents using 113Cd-NMR spectroscopy. Chem Res Toxicol. 1992,5:568-75. Abstract only.

Becker et al., NO-independent regulatory site of direct sGC stimulators like YC-1 and BAY 41/2272. BMC Pharmacol. 2001;1:13. Epub Dec. 28, 2001.

Berman et al., Sensitization and catalysis of light-induced decarbonylation of aldehydes. J Am Chem Soc. 1963;85(24):4010-4013.

Beutler, The effect of carbon monoxide on red cell life span in sickle cell disease. Blood. Aug. 1975;46(2):253-9.

Boissiere et al., Exercise and vasorelaxing effects of CO-releasing molecules in hypertensive rats. Med Sci Sports Exerc. Apr. 2006;38(4):652-9.

Botros et al., Interaction between endogenously produced carbon monoxide and nitric oxide in regulation of renal afferent arterioles. Am J Physiol Heart Circ Physiol. Dec. 2006;291(6):H2772-8. Epub Jul. 14, 2006.

Brashears et al., Effect of meat packaging technologies on the safety and spoilage-indicating characteristics of ground beef—Phase 1: safety characteristics. 2006. National Cattleman's Beef Asscoiation. 22 pages. Available at www.fda.gov/ohrms/dockets/dockets/05p0459/05p-0459-c000009-01-vol2.pdf.

Brooks et al., The spoilage characteristics of ground beef packaged in high-oxygen and low-oxygen modified atmosphere packages. Proc. Reciprocal Meat Conference. University of Illinois at Urbana-Champaign. 2006:61-5.

Brouard et al., Carbon monoxide generated by heme oxygenase 1 suppresses endothelial cell apoptosis. J Exp Med. Oct. 2, 2000;192(7):1015-26.

Brüne et al., Inhibition of platelet aggregation by carbon monoxide is mediated by activation of guanylate cyclase. Mol Pharmacol. Oct. 1987;32(4):497-504.

Bundgaard et al., Pro-drugs as delivery systems. Pharm Int. 1981;2:136-40.

Bundgaard et al., Pro-drugs as drug delivery systems XX. Oxazolidines as potential pro-drug types for β-aminoalcohols, aldehydes or ketones. Intl J Pharm. Feb. 1982;10(2):165-75. Abstract only.

Burgmayer et al., Synthesis and structure of a 7-coordinate molybdenum carbonyl fluoride derivative—Et4n Mo(Co)2(S2cnet2)2f. Inorganic Chem. 1985;24:2224-30.

Campbell et al., Molecular targets in immune-mediated diseases: the case of tumour necrosis factor and rheumatoid arthritis. Immunol Cell Biol. Oct. 2003;81(5):354-66.

Cepinskas et al., Carbon monoxide liberated from carbon monoxide-releasing molecule CORM-2 attenuates inflammation in the liver of septic mice. Am J Physiol Gastrointest Liver Physiol, Jan. 2008; 294:G184-G191.

Chakravortty et al., Inducible nitric oxide synthase and control of intracellular bacterial pathogens. Microbes Infect. Jun. 2003;5(7):621-7. Review. Abstract only.

Chatterjee, Water-soluble carbon monoxide-releasing molecules: helping to elucidate the vascular activity of the 'silent killer'. Br J Pharrnacol. Jun. 2004;142(3):391-3. Epub May 17, 2004.

Chauveau et al., Gene transfer of heme oxygenase-1 and carbon monoxide delivery inhibit chronic rejection. Am J Transplant. Aug. 2002;2(7):581-92.

Chlopicki et al., Carbon monoxide released by CORM-3 inhibits human platelets by a mechanism independent of soluble guanylate cyclase. Cardiovasc Res. Jul. 15, 2006;71(2):393-401. Epub Mar. 22, 2006.

Cihonski et al., Crown ethers in inorganic chemistry—preparation and characterization of group 6 pentacarbonyl hydroxides and fluorides. Inorganic Chem. 1975;14:1717-20.

Clark et al., Cardioprotective actions by a water-soluble carbon monoxide-releasing molecule. Circ Res. Jul. 25, 2003;93(2):e2-8. Epub Jul. 3, 2003.

Clark et al., Heme oxygenase-1-derived bilirubin ameliorates postischemic myocardial dysfunction. Am J Physiol Heart Circ Physiol. Feb. 2000;278(2):H643-51.

Clark et al., Measuring left ventricular function in the normal, infarcted and CORM-3-preconditioned mouse heart using complex admittance-derived pressure volume loops. J Pharmacol Methods. Mar.-Apr. 2009;59(2):94-9.

Coceani et al., Carbon monoxide formation in the ductus arteriosus in the lamb: implications for the regulation of muscle tone. Br J Pharmacol. Feb. 1997;120(4):599-608.

Coceani, Carbon monoxide in vasoregulation: the promise and the challenge. Circ Res. Jun. 23, 2000;86(12):1184-6. Review.

Cohen et al., Dithiobenzoatotetracarbonylmanganese(I). Inorg Chem. 1964;3(11):1641-42.

Conant et al., Trimethylacetaldehyde and dimethylethylacetaldehyde. J Am Chem Soc. 1929;51(4):1246-55.

Cotton et al., Dimethyl- and diethyldithiocarbamate complexes of some metal carbonyl compounds. Inorg Chem. Jun. 2, 1964;3:1398-1402.

Cotton et al., X-ray molecular structures of Mn(CO)5(O2CCF3) and Mn(CO)3(C5H5N)2(O2CCF3). Inorg Chem. 1981;20(4):1287-91.

Coville et al., Steric measurement of substituted cyclopentadiene ligands and the synthesis and proton NMR spectral analysis of [(.eta.5-C5H4R)Fe(CO)(L)I] complexes with variable R. Organometallics. 1992;11(3):1082-90.

De Backer et al., Role of the soluble guanylyl cyclase alpha1/alpha2 subunits in the relaxant effect of CO and CORM-2 in murine gastric fundus. Naunyn Schmiedebergs Arch Pharmacol. Nov. 2008;378(5):493-502. Epub Jun. 18, 2008.

De Backer et al., Water-soluble CO-releasing molecules reduce the development of postoperative ileus via modulation of MAPK/HO-1 signalling and reduction of oxidative stress. Gut. Mar. 2009;58(3):347-56. Epub Nov. 20, 2008.

De Filippo et al., Inductive effect in dithiocarbanate decomposition mechanism. J Org Chem. 1973;38(3):560-3.

Desmard et al., A carbon monoxide-releasing molecule (CORM-3) exerts bactericidal activity against *Pseudomonas aeruginosa* and improves survival in an animal model of bacteraemia. FASEB J. Apr. 2009;23(4):1023-31. Epub Dec. 18, 2008.

Desmard et al., Carbon monoxide reduces the expression and activity of matrix metalloproteinases 1 and 2 in alveolar epithelial cells. Cell Mol Biol (Noisy-le-grand). Sep. 30, 2005;51(4):403-8.

Dharmaraj et al., Ruthenium (II) complexes containing bidentate Schiff bases and their antifungal activity. Transition Metal Chemistry. 2001; 26(1-2): 105-109.

Di Pascoli et al., Chronic Co levels have [corrected] a beneficial effect on vascular relaxation in diabetes. Biochem Biophys Res Commun. Feb. 17, 2006;340(3):935-43. Epub Dec. 27, 2005. Erratum in: Biochem Biophys Res Commun. Mar. 14, 2006;342(3):1003.

Douglas et al., Preparation of some group Vi fluorometal carbonyl derivatives. J Organometal Chem. 1974;65:65-9.

Drew et al., Synthesis, spectral properties, and reactions of manganese and rhenium pentacarbonyl phosphine and phosphite cation derivatives and related complexes. Inorg. Chem. 1975;14(7):1579-84.

Dröge, Free radicals in the physiological control of cell function. Physiol Rev. Jan. 2002;82(1):47-95. Review.

Duchêne et al., Cyclodextrins in targeting. Application to nanoparticles. Adv Drug Deliv Rev. Mar. 1, 1999;36(1):29-40.

Duckers et al., Heme oxygenase-1 protects against vascular constriction and proliferation. Nat Med. Jun. 2001;7(6):693-8.

Egli et al., Organometallic 99mTc-aquaion labels peptide to an unprecedented high specific activity. J Nucl Med. Nov. 1999;40(11):1913-7.

El-Sayed et al., Catalysis by crown ether complexes—part III effect of cation on the catalytic activity of crown ether—alkali metal halide complexes in the liquid phase oxidation of ethylbenzene. Egypt J Chem. 1979;22(1):23-8.

Elliott et al., Nitric oxide: a regulator of mucosal defense and injury. J Gastroenterol. Dec. 1998;33(6):792-803. Review. Abstract only.

Fairlamb et al., η4-pyrone iron(0)carbonyl complexes as effective CO-releasing molecules (CO-RMs). Bioorg Med Chem Lett. Feb. 15, 2006;16(4):995-8. Epub Nov. 11, 2005.

Fang, Antimicrobial reactive oxygen and nitrogen species: concepts and controversies. Nat Rev Microbiol. Oct. 2004;2(10):820-32. Review. Abstract only.

Feldmann et al., Anti-TNF alpha therapy of rheumatoid arthritis: what have we learned? Annu Rev Immunol. 2001;19:163-96. Review.

Ferrándiz et al., Treatment with a CO-releasing molecule (CORM-3) reduces joint inflammation and erosion in murine collagen-induced arthritis. Ann Rheum Dis. Sep. 2008;67(9):1211-7. Epub Dec. 6, 2007.

Fischer et al., Methylpyridin-Chrom(O)-Tricarbonyl. Zeitschrift Fur Naturforschung Part-B-Chemie Biochemie Biophysik Biologie Und Verwandten Gebiete. 1959;14:736-7.

Fischer et al., Uber aromatenkomplexe von metallen .37. zur aromatenkomplexebildung des pyridins mit chromhexacarbonyl. Chemische berichte-recueil. 1960;93:1156-61. English abstract provided.

Fischer, Crystal structure of 1,4,7,10,13-pentaoxacylcopentadecane sodium bromide, C10H20BrNaO5. Zeitschrift fur kristallographie. 1996;2001.827-8.

Fiumana et al., Carbon monoxide mediates vasodilator effects of glutamate in isolated pressurized cerebral arterioles of newborn pigs. Am J Physiol Heart Circ Physiol. Apr. 2003;284(4):H1073-9.

Foresti et al., Reviewing the use of carbon monoxide-releasing molecules (CO-RMs) in biology: implications in endotoxin-mediated vascular dysfunction. Cell Mol Biol (Noisy-le-grand). Sep. 30, 2005;51(4):409-23.

Foresti et al., The heme oxygenase pathway and its interaction with nitric oxide in the control of cellular homeostasis. Free Radic Res. Dec. 1999;31(6):459-75. Review.

Foresti et al., Vasoactive properties of CORM-3, a novel water-soluble carbon monoxide-releasing molecule. Br J Pharmacol. Jun. 2004;142(3):453-60. Epub May 17, 2004.

Frangogiannis et al., The inflammatory response in myocardial infarction. Cardiovasc Res. Jan. 2002;53(1):31-47. Review.

Friebe et al., Sensitizing soluble guanylyl cyclase to become a highly CO-sensitive enzyme. EMBO J. Dec. 16, 1996;15(24):6863-8.

Friebe et al., YC-1 potentiates nitric oxide- and carbon monoxide-induced cyclic GMP effects in human platelets. Mol Pharmacol. Dec. 1998;54(6):962-7.

Fujita et al., Paradoxical rescue from ischemic lung injury by inhaled carbon monoxide driven by derepression of fibrinolysis. Nat Med. May 2001;7(5):598-604.

Fukuda et al., Induction of heme oxygenase-1 (HO-1) after traumatic brain injury in the rat. Neurosci Lett. Oct. 20, 1995;199(2):127-30.

Giboreau et al., Procedure for the preparation of pure dithiocarbamates. J Org Chem. 1994;59:1205-7.

Greener, Now you're signaling, with gas: gasotransmitters open a window on biology and drug development. The Scientist. 2004;18(17):20.

Guo et al., Administration of a CO-releasing molecule at the time of reperfusion reduces infarct size in vivo. Am J Physiol Heart Circ Physiol. May 2004;286(5):H1649-53. Epub Jan. 2, 2004.

Günther et al., Carbon monoxide protects pancreatic beta-cells from apoptosis and improves islet function/survival after transplantation. Diabetes. Apr. 2002;51(4):994-9. MEDLINE Abstract.

Haag et al., Polymer therapeutics: concepts and applications. Angew Chem Int Ed Engl. Feb. 13, 2006;45(8):1198-215. Review. Abstract only.

Haddleton et al., [N-Alkyl-(2-pyridyl)methanimine]copper(I) complexes: characterisation and application as catalysts for atom-transfer polymerisation. Dec. 7, 1998;1998(11):1799-1806. Abstract only.

Haddleton et al., Atom transfer polymerization of methyl methacrylate mediated by alkylpyridylmethanimine type ligands, copper(I) bromide, and alkyl halides in hydrocarbon solution. Macromolecules. 1999;32(7):2110-19. Abstract only.

Hadjigogos, The role of free radicals in the pathogenesis of rheumatoid arthritis. Panminerva Med. Mar. 2003;45(1):7-13. Review. Abstract only.

Hall et al., DNA interaction with metal complexes and salts of substituted boranes and hydroborates in murine and human tumor cell lines. Anticancer Drugs. Aug. 1991;2(4):389-99.

Hall et al., The anti-inflammatory activity of boron derivatives in rodents. Met Based Drugs. 1995;2(1):1-12.

Hall et al., The anti-inflammatory activity of metal complexes and salts of amine carboxyboranes. Appl Organomett Chem. 1994;8:473-80.

Hall et al., The hypolipidemic activity of metal complexes of amine carboxyboranes in rodents. Met Based Drugs. 1994;1(4):329-36.

Hancock et al., Antibody-induced transplant arteriosclerosis is prevented by graft expression of anti-oxidant and anti-apoptotic genes. Nat Med. Dec. 1998;4(12):1392-6.

Henricks et al., Reactive oxygen species as mediators in asthma. Pulm Pharmacol Ther. 2001;14(6):409-20. Review. Abstract only.

Hieber et al., Derivate des Mangancarbonyls mit schwefelorganischen Liganden. Chemische Berichte. 1966;99(7):2312-21.

Hitchon et al., Oxidation in rheumatoid arthritis. Arthritis Res Ther. 2004;6(6):265-78. Epub Oct. 13, 2004. Review.

Hogg, Free radicals in disease. Semin Reprod Endocrinol. 1998;16(4):241-8. Review. Abstract only.

Hosgood et al., Application of nitric oxide and carbon monoxide in a model of renal preservation. Br J Surg. Aug. 2008;95(8):1060-7.

Ignat'ev et al., Reactivity of perfluoroakyl halides towards nucleophiles. Russ J Electrochem. 1995;31(12):1235-9. Translated from Elektrokhimiya. 1995:31(12):1337-42.

Ioganson et al., Metal carbonyl complexes with ligands of biological origin. Russ Chem Rev. 1985;54(3):277-92.

Jander et al., Neutralisationenanaloge reaktionen in essigaureanhybrid. Zietschrift fur anorganische chemie. 1948;255:238-52. English abstract provided.

Jellum et al., Quantitative determination of biologically important thiols and disulfides by gas-liquid chromatography. Analyt Biochem. 1969;31:339-47. Abstract only.

Johansen et al., Spectrophotometric determination of the rates of hydrolysis of aldehyde-releasing pro-drugs in aqueous solution and plasma. Intl J Pharma. Dec. 1982;13(1):89-98. Abstract only.

Johnson et al., Metal carbonyls as pharmaceuticals? [Ru(CO)3CI(glycinate)], a CO-releasing molecule with an extensive aqueous solution chemistry. Dalton Trans. Apr. 21, 2007;(15):1500-8. Epub Mar. 8, 2007.

Johnson et al., Metal carbonyls: a new class of pharmaceuticals? Angew Chem Int Ed Engl. Aug. 18, 2003;42(32):3722-9.

Johnson et al., Role of endogenous carbon monoxide in central regulation of arterial pressure. Hypertension. Oct. 1997;30(4):962-7.

Józkowicz et al., Heme oxygenase and angiogenic activity of endothelial cells: stimulation by carbon monoxide and inhibition by tin protoporphyrin-IX. Antioxid Redox Signal. Apr. 2003;5(2):155-62.

Kamimura et al., The protective effect of carbon monoxide on the ischemia-induced cell death. The J Biochem. Aug. 2002;74(8):926. Japanese abstract. English translation provided.

Kharitonov et al., Basis of guanylate cyclase activation by carbon monoxide. Proc Natl Acad Sci U S A. Mar. 28, 1995;92(7):2568-71.

Kharitonov et al., Kinetics and equilibria of soluble guanylate cyclase ligation by CO: effect of YC-1. Biochemistry. Aug. 17, 1999;38(33):10699-706.

Krueger et al., Potential of tumor necrosis factor inhibitors in psoriasis and psoriatic arthritis. Arch Dermatol. Feb. 2004;140(2):218-25. Review.

Kubic et al., Metabolism of dihalomethanes to carbon monoxide. I. In vivo studies. Drug Metab Dispos. Jan.-Feb. 1974;2(1):53-7. Abstract only.

Kuiate et al., Composition of the essential oil from leaves and flowers of *Dichrocephala integrifolia* (L.) O. Kuntze Chev. From Cameroon. Flavour and Fragrance J. Nov./Dec. 1999;14(6):419-20. Abstract only.

Lambert et al., O,O'-Diphenyldithiophosphatotetracarbonylmanganese(I) and related compounds. Inorg Chem. 1966;5(7):1287-9.

Ledger, Carbon monoxide-releasing metal carbonyls: a new class of pharmaceuticals? Drug Disc Today. 2003;8:1096.

Lee et al., Heme oxygenase-1 mediates the anti-inflammatory effect of interleukin-10 in mice. Nat Med. Mar. 2002;8(3):240-6.

Levrand et al., Controlled release of volatile aldehydes and ketones by reversible hydrazone formation—classical profragrances are getting dynamic. Chem. Commun. 2006;28:2965-7.

Li et al., Carbon monoxide protects PC12 cells from peroxynitrite-induced apoptotic death by preventing the depolarization of mitochondrial transmembrane potential. Biochem Biophys Res Commun. Apr. 14, 2006;342(3):984-90.

Lipmann et al., Organometallic Lewis Acids. LI. Reactivity of organometallic Lewis Acids (OC)4Re(Oet2)FBF3 and (OC)2(PPh3)2Ru(FBF3)2. Journal of Organometallic Chemistry. 1994;466(1-2):167-174. English abstract provided.

Loftsson et al., Cyclodextrins in topical drug formulations: theory and practice. Int J Pharm. Aug. 28, 2001;225(1-2):15-30. Review.

Lovell et al., Biologic agents for the treatment of juvenile rheumatoid arthritis: current status. Paediatr Drugs. 2004;6(3):137-46.

Mahmoud et al., Potential anticancer agents. XVI. Isolation of bicyclofarnesane sesquiterpenoids from *Capsicodendron dinisii*. J Nat Prod. May-Jun. 1980;43(3):365-71. Abstract only.

Marks et al., Does carbon monoxide have a physiological function? Trends Pharmacol Sci. May 1991;12(5):185-8. Review.

Martins et al., Induction of carbon monoxide in the donor reduces graft immunogenicity and chronic graft deterioration. Transplant Proc. Jan.-Feb. 2005;37(1):379-81.

Matsuda et al., Mediators of non-adrenergic non-cholinergic inhibitory neurotransmission in porcine jejunum. Neurogastroenterol Motil. Oct. 2004;16(5):605-12.

Mattes et al., Triply bridged thiobenzoato carbonyl manganates(I) and rhenates(I). The crystal and molecular structure of caesium tris(μ-thiobenzoatos(S))bis(tricarbonyl rhenate). J Organometall Chem. Sep. 25, 1979; 178(1):191-6.

McLaughlin et al., Potentiation of carbon monoxide-induced relaxation of rat aorta by YC-1 [3-(5'-hydroxymethyl-2'-furyl)-1-benzylindazole]. Can J Physiol Pharmacol. Apr. 2000;78(4):343-9.

McMillen et al., Hydrocarbon bond dissociation energies. Ann Rev Phys Chem. Oct. 1982;33:493-532.

Meder et al., Metallkomplexe mit biologisch wichtigen liganden, XLII [1] carbonylmetallkomplexe mit anionen von mehrfunktionellen alpha-aminosaeuren [Metal complexes with biologically important ligands], XLII [1] carbonyl metal complexes with anions of polyfunctional alpha-amino acids. Zeitschrift fur Naturforschung;1986:1247-54. German language reference. English abstract provided.

Megías et al., The carbon monoxide-releasing molecule tricarbonyldichlororuthenium(II) immer protects human osteoarthritic chondrocytes and cartilage from the catabolic actions of interleukin-1beta. J Pharmacol Exp Ther. Apr. 2008;325(1):56-61. Epub Jan. 14, 2008.

Miguel et al., Manganese(I) complexes with (tricyclohexylphosphonio)dithiocarboxylate as chelate and unidentate ligand. X-Ray crystal structure of fac-[Mn(CO)3(S2CP(C6H11)3}2]ClO4oH2O. J Chem Soc, Dalton Trans. 1987;12:2875-80.

Mikuls et al., Benefit-risk assessment of infliximab in the treatment of rheumatoid arthritis. Drug Saf. 2003;26(1):23-32. Review. Abstract only.

Miller et al., The pharmacological activities of the metabolites of N-[(trimethylamineboryl)-carbonyl]-phenylalanine methyl ester. Met Based Drugs. 1996;3(5):219-26.

Moncada et al., Nitric oxide: physiology, pathophysiology, and pharmacology. Pharmacol Rev. Jun. 1991;43(2):109-42.

Moncada et al., The discovery of nitric oxide and its role in vascular biology. Br J Pharmacol. Jan. 2006;147 Suppl 1:S193-201.

Moore et al., Brief inhalation of low-dose carbon monoxide protects rodents and swine from postoperative ileus. Crit Care Med. Jun. 2005;33(6):1317-26.

Morita et al., Carbon monoxide controls the proliferation of hypoxic vascular smooth muscle cells. J Biol Chem. Dec. 26, 1997;272(52):32804-9.

Morita et al., Endothelial cell expression of vasoconstrictors and growth factors is regulated by smooth muscle cell-derived carbon monoxide. J Clin Invest. Dec. 1995;96(6):2676-82.

Morse et al., Suppression of inflammatory cytokine production by carbon monoxide involves the JNK pathway and AP-1. J Biol Chem. Sep. 26, 2003;278(39):36993-8. Epub Jul. 11, 2003.

Motterlini et al., Bioactivity and pharmacological actions of carbon monoxide-releasing molecules. Curr Pharm Des. 2003;9(30):2525-39.

Motterlini et al., Chapter 16: Studies on the development of carbon-monoxide—releasing molecules: potential applications for the treatment of cardiovascular dysfunction. Ed., Rui Wang. CRC Press, New York. 2002:249-72.

Motterlini et al., CORM-A1: a new pharmacologically active carbon monoxide-releasing molecule. FASEB J. Feb. 2005;19(2):284-6. Epub Nov. 19, 2004.

Motterlini et al., Therapeutic applications of carbon monoxide-releasing molecules. Expert Opin Investig Drugs. Nov. 2005;14(11):1305-18. Review.

Motterlini, Vasoactive properties of carbon monoxide-releasing molecules. Biomed Pharmacother. 2002;56(7):349-50.

Moya et al., Metal carbonyl complexes containing heterocyclic nitrogen ligands: Part IX. MnBr(CO)3(3,3?-R-2,2?-biquinoline) compounds. Polyhedron. Mar. 1, 2002; 21(4):439-44. Abstract only.

Mungrue et al., From molecules to mammals: what's NOS got to do with it? Acta Physiol Scand. Oct. 2002;179(2):123-35. Review. Abstract only.

Musameh et al., Improved myocardial function after cold storage with preservation solution supplemented with a carbon monoxide-releasing molecule (CORM-3). J Heart Lung Transplant. Nov. 2007;26(11):1192-8.

Musameh et al., Positive inotropic effects of carbon monoxide-releasing molecules (CO-RMs) in the isolated perfused rat heart. Br J Pharmacol. Dec. 2006;149(8):1104-12. Epub Oct. 23, 2006.

Nakao et al., Carbon monoxide inhalation protects rat intestinal grafts from ischemia/reperfusion injury. Am J Pathol. Oct. 2003;163(4):1587-98.

Nakao et al., Protective effect of carbon monoxide in transplantation. J Cell Mol Med. Jul.-Sep. 2006;10(3):650-71. Review.

Nathan, Points of control in inflammation. Nature. Dec. 19-26, 2002;420(6917):846-52. Review.

Ndisang et al., Modulation of the immunological response of guinea pig mast cells by carbon monoxide. Immunopharmacology. Jun. 1999;43(1):65-73.

Neto et al., Protection of transplant-induced renal ischemia-reperfusion injury with carbon monoxide. Am J Physiol Renal Physiol. Nov. 2004;287(5):F979-89. Epub Aug. 3, 2004.

Nitschke et al., Properties of (trifluoromethanesulfonato)pentacarbonylmanganese(I) and—rhenium(I). Reactions in superacid solvents. Inorg Chem. 1985;24(13):1972-8.

Nobre et al., Antimicrobial action of carbon monoxide-releasing compounds. Antimicrob Agents Chemother. Dec. 2007;51(12):4303-7. Epub Oct. 8, 2007.

Nudelman et al., Prodrugs of butyric acid. Novel derivatives possessing increased aqueous solubility and potential for treating cancer and blood diseases. Eur J Med Chem. Jan. 2001;36(1):63-74. Abstract only.

Nudelman et al., The role of intracellularly released formaldehyde and butyric acid in the anticancer activity of acyloxyalkyl esters. J. Med. Chem.. Jan. 22, 2005;48(4):1042-54. Abstract only.

O'Brien et al., Aldehyde sources, metabolism, molecular toxicity mechanisms, and possible effects on human health. Crit Rev Toxicol. Aug. 2005;35(7):609-62. Review.

Otterbein et al., Carbon monoxide has anti-inflammatory effects involving the mitogen-activated protein kinase pathway. Nat Med. Apr. 2000;6(4):422-8.

Otterbein et al., Carbon monoxide suppresses arteriosclerotic lesions associated with chronic graft rejection and with balloon injury. Nat Med. Feb. 2003;9(2):183-90. Epub Jan. 21, 2003.

Otterbein et al., Heme oxygenase-1: unleashing the protective properties of heme. Trends Immunol. Aug. 2003;24(8):449-55. Review.

Otterbein, Carbon monoxide: innovative anti-inflammatory properties of an age-old gas molecule. Antioxid Redox Signal. Apr. 2002;4(2):309-19. Review.

Ozawa et al., Leydig cell-derived heme oxygenase-1 regulates apoptosis of premeiotic germ cells in response to stress. J Clin Invest. Feb. 2002;109(4):457-67.

Pae et al., Carbon monoxide produced by heme oxygenase-1 suppresses T cell proliferation via inhibition of IL-2 production. J Immunol. Apr. 15, 2004;172(8):4744-51.

Paintner et al., Synthesis and antimicrobial activity of tetrodecamycin partial structures. Bioorg Med Chem. Jul. 3, 2003;11(13):2823-33. Abstract only.

Pankey et al., Clinical relevance of bacteriostatic versus bactericidal mechanisms of action in the treatment of Gram-positive bacterial infections. Clin Infect Dis. Mar. 15, 2004;38(6):864-70. Epub Mar. 1, 2004. Review.

Patel et al., Preparation of ($\eta$5-cyclopentadienyl) and ($\eta$5-Methylcyclopentadienyl)Fe(CO)2Me cyclodextrin inclusion compounds and their subsequent ligand substitution reactions. Attempts at cyclodextrin mediated enantioselective ligand substitution. J Organometal Chem. 1997;547:103-112.

Peloso et al., Expanding the armamentarium for the spondyloarthropathies. Arthritis Res Ther. 2004;6 Suppl 2:S36-43. Epub Jun. 21, 2004.

Piantadosi, Biological chemistry of carbon monoxide. Antioxid Redox Signal. Apr. 2002;4(2):259-70. Review.

Quick et al., Pentacarbonylmanganese halides. In Inorganic Syntheses, vol. 19. Duward F. Shriver., Ed. Inorganic Syntheses, Inc. 1979:158-63.

Rattan et al., Mechanism of internal anal sphincter relaxation by CORM-1, authentic CO, and NANC nerve stimulation. Am J Physiol Gastrointest Liver Physiol. Sep. 2004;287(3):G605-11.

Rehder et al., 55Mn NMR characteristics of carbonylmanganese complexes with hetero-substituted dithioformato-, thioformamido- and thioformamide ligands [1]. Inorg Chim Acta. 1983;73:243-7. Abstract only.

Reimann et al., Reactions of metal carbonyls. Part III. Steric and stereochemical limitations of higher substitution of manganese carbonyl bromide. J Chem Soc Dalton Trans. 1973;841-6. Abstract only.

Rodella et al., Carbon monoxide and biliverdin prevent endothelial cell sloughing in rats with type I diabetes. Free Radic Biol Med. Jun. 15, 2006;40(12:2198-205. Epub Mar. 20, 2006.

Rutkowska-Zbik et al., Theoretical density functional theory studies on interactions of small biologically active molecules with isolated heme group. J Comput Chem. Mar. 2007;28(4):825-31.

Ryan et al., Renal vascular responses to CORM-A1 in the mouse. Pharmacol Res. Jul. 2006;54(1):24-9. Epub Mar. 9, 2006.

Ryter et al., Carbon monoxide in biology and medicine. Bioessays. Mar. 2004;26(3):270-80.

Ryter et al., Carbon monoxide: to boldly go where NO has gone before. Sci STKE. Apr. 20, 2004;2004(230):RE6. Review.

Ryter et al., Heme oxygenase-1/carbon monoxide: from basic science to therapeutic applications. Physiol Rev. Apr. 2006;86(2):583-650. Review.

Ryter et al., Heme oxygenase/carbon monoxide signaling pathways: regulation and functional significance. Mol Cell Biochem. May-Jun. 2002;234-235(1-2):249-63. Review.

Sacerdoti et al., Treatment with tin prevents the development of hypertension in spontaneously hypertensive rats. Science. Jan. 20, 1989;243(4889):388-90.

Salazar-Salinas et al., Molecular biosensor based on a coordinated iron complex. J Chem Phys. Mar. 14, 2009;130(10):105101.

Sandborn, Strategies for targeting tumour necrosis factor in IBD. Best Pract Res Clin Gastroenterol. Feb. 2003;17(1):105-17. Review.

Sandouka et al., Carbon monoxide-releasing molecules (CO-RMs) modulate respiration in isolated mitochondria. Cell Mol Biol (Noisy-le-grand). Sep. 30, 2005;51(4):425-32.

Sandouka et al., Treatment with CO-RMs during cold storage improves renal function at reperfusion. Kidney Int. Jan. 2006;69(2):239-47.

Sarady et al., Carbon monoxide protection against endotoxic shock involves reciprocal effects on iNOS in the lung and liver. FASEB J. May 2004;18(7):854-6. Epub Mar. 4, 2004.

Sawle et al., Carbon monoxide-releasing molecules (CO-RMs) attenuate the inflammatory response elicited by lipopolysaccharide in RAW264.7 murine macrophages. Br J Pharmacol. Jul. 2005;145(6):800-10.

Sawle et al., Homocysteine attenuates endothelial haem oxygenase-1 induction by nitric oxide (NO) and hypoxia. FEBS Lett. Nov. 23, 2001;508(3):403-6.

Schmidt et al., Manganese(I) and rhenium(I) pentacarbonyl(Trifluoromethanesulfatonato) complexes. In Inorganic Syntheses, Ed. Herbert D. Kaesz. Inorganic Syntheses, Inc. 1989:113-7.

Severin et al., Metal complexes of biologically important ligands. LXX. Synthesis, stereochemistry and reactions of ruthenium (II) and osmium (II) complexes with .alpha.-amino carboxylates. 1994; 127(4): 615-620.

Shapiro, Carbonyl-trapping therapeutic strategies. Am J Ther. Sep. 1998;5(5):323-53. Review.

Shiohira et al., Protective effect of carbon monoxide donor compounds in endotoxin-induced acute renal failure. Am J Nephrol. 2007;27(5):441-6. Epub Jul. 12, 2007.

Siow et al., Heme oxygenase-carbon monoxide signalling pathway in atherosclerosis: anti-atherogenic actions of bilirubin and carbon monoxide? Cardiovasc Res. Feb. 1999;41(2):385- 94.

Skattebøl et al., Synthesis of (±)-Lineatin, an aggregation pheromone component of Trypodendron lineatum. Acta Chem Scand B. 1985;39:291-304.

Song et al., Carbon monoxide inhibits human airway smooth muscle cell proliferation via mitogen-activated protein kinase pathway. Am J Respir Cell Mol Biol. Nov. 2002;27(5):603-10.

Song et al., Carbon monoxide inhibits T lymphocyte proliferation via caspase-dependent pathway. J Immunol. Jan. 15, 2004;172(2):1220-6.

Spector, Review: Oxidative stress and disease. J Ocul Pharmacol Ther. Apr. 2000;16(2):193-201. Review. Abstract only.

Srisook et al., CO from enhanced HO activity or from CORM-2 inhibits both O2- and NO production and downregulates HO-1 expression in LPS-stimulated macrophages. Biochem Pharmacol. Jan. 12, 2006;71(3):307-18. Epub Dec. 2, 2005.

Srisook et al., Role of NO in enhancing the expression of HO-1 in LPS-stimulated macrophages. Methods Enzymol. 2005;396:368-77.

Staal et al., The syntheses and coordination properties of M(CO)3X(DAB) (M = Mn, Re; X = CI, Br, I; DAB = 1,4-diazabutadiene). J Organometal Chem. May 1, 1979:170( 2):235-45. Abstract only.

Stagni et al., A water-soluble carbon monoxide-releasing molecule (CORM-3) lowers intraocular pressure in rabbits. Br J Ophthalmol. Feb. 2009;93(2):254-7. Epub Oct. 31, 2008.

Stanford et al., Carbon monoxide inhibits endothelin-1 release by human pulmonary artery smooth muscle cells. Eur J Pharmacol. Feb. 23, 2004;486(3):349-52.

Stanford et al., Heme oxygenase is expressed in human pulmonary artery smooth muscle where carbon monoxide has an anti-proliferative role. Eur J Pharmacol. Jul. 25, 2003;473(2-3):135-41.

Stec et al., Heme oxygenase-1 induction does not improve vascular relaxation in angiotensin II hypertensive mice. Am J Hypertens. Feb. 2008;21(2):189-93. Epub Jan. 3, 2008.

Stein et al., Administration of a CO-releasing molecule induces late preconditioning against myocardial infarction. J Mol Cell Cardiol. Jan. 2005;38(1):127-34. Epub Dec. 8, 2004.

Stone et al., Soluble guanylate cyclase from bovine lung: activation with nitric oxide and carbon monoxide and spectral characterization of the ferrous and ferric states. Biochemistry. May 10, 1994;33(18):5636-40.

Stone et al., Synergistic activation of soluble guanylate cyclase by YC-1 and carbon monoxide: implications for the role of cleavage of the iron-histidine bond during activation by nitric oxide. Chem Biol. May 1998;5(5):255-61.

Suematsu et al., Carbon monoxide: an endogenous modulator of sinusoidal tone in the perfused rat liver. J Clin Invest. Nov. 1995;96(5):2431-7.

Sun et al., Attenuation of leukocytes sequestration by carbon monoxide-releasing molecules: liberated carbon monoxide in the liver of thermally injured mice. J Burn Care Res. Jan.-Feb. 2007;28(1):173-81.

Sun et al., CO-releasing molecules (CORM-2)-liberated CO attenuates leukocytes infiltration in the renal tissue of thermally injured mice. Int J Biol Sci. Jun. 16, 2008;4(3):176-83.

Sun et al., Preconditioning of carbon monoxide releasing molecule-derived CO attenuates LPS-induced activation of HUVEC. Int J Biol Sci. Aug. 22, 2008;4(5):270-8.

Sun et al., Role of CO-releasing molecules liberated CO in attenuating leukocytes sequestration and inflammatory responses in the lung of thermally injured mice. J Surg Res. May 1, 2007;139(1):128-35. Epub Feb. 9, 2007.

Suzuki et al., Activated platelets in ulcerative colitis enhance the production of reactive oxygen species by polymorphonuclear leukocytes. Scand J Gastroenterol. Dec. 2001;36(12):1301-6. Abstract only.

Szallasi et al., Dialdehyde sesquiterpenes and other terpenoids as vanilloids. Eur J Pharmacol. Aug. 28, 1998;356(1):81-9. Abstract only.

Taillé et al., Mitochondrial respiratory chain and NAD(P)H oxidase are targets for the antiproliferative effect of carbon monoxide in human airway smooth muscle. J Biol Chem. Jul. 8, 2005;280(27):25350-60. Epub Apr. 29, 2005.

Tayem et al., Protection against cisplatin-induced nephrotoxicity by a carbon monoxide-releasing molecule. Am J Physiol Renal Physiol. Apr. 2006;290(4):F789-94. Epub Nov. 15, 2005.

Tilg et al., Antitumour necrosis factor therapy in Crohn's disease. Expert Opin Biol Ther. Oct. 2002;2(7):715-21. Review. Abstract only.

Togane et al., Protective roles of endogenous carbon monoxide in neointimal development elicited by arterial injury. Am J Physiol Heart Circ Physiol. Feb. 2000;278(2):H623-32.

Treichel et al., Synthesis and reactivity of bridging thiolato-manganese carbonyl complexes, Et4N[Mn2(µ-SR)3(CO)6]. J Organometall Chem. Sep. 10, 1985;292(3):385-93.

Urwyler et al., Positive allosteric modulation of native and recombinant gamma-aminobutyric acid(B) receptors by 2,6-Di-tert-butyl-4-(3-hydroxy-2,2-dimethyl-propyl)-phenol (CGP7930) and its aldehyde analog CGP13501. Mol Pharmacol. Nov. 2001;60(5):963-71.

Van Staveren et al., Spectroscopic Properties, Electrochemistry, and Reactivity of Mo0, MoI, and MoII Complexes with the [Mo(bpa)(CO)3] Unit [bpa = bis(2-picolyl)amine] and Their Application for the Labelling of Peptides. Eur J lnorg Chem. 2002;6:1518-29.

Vannacci et al., Evaluation of the effects of a novel carbon monoxide releasing molecule (CORM-3) in an in vitro model of cardiovascular inflammation. 1. Histamine in allergy, inflammation, tissue growth and repair. Inflamm Res. Apr. 2006;55 Suppl 1:S05-6.

Vannacci et al., The effect of a carbon monoxide-releasing molecule on the immunological activation of guinea-pig mast cells and human basophils. Inflamm Res. 2004;53 Suppl 53:S09-10.

Varadi et al., Beneficial effects of carbon monoxide-releasing molecules on post-ischemic myocardial recovery. Life Sci. Apr. 3, 2007;80(17):1619-26. Epub Feb. 2, 2007.

Vera et al., Protective effect of carbon monoxide-releasing compounds in ischemia-induced acute renal failure. J Am Soc Nephrol. Apr. 2005;16(4):950-8. Epub Feb. 23, 2005.

Verma et al., Carbon monoxide: a putative neural messenger. Science. Jan. 15, 1993;259(5093):381-4.

Verona et al., Regioselectivity in the nucleophilic functionalization of xanthene complexes of Mn(CO)3. J Organelle Chem. Nov. 1, 1996;524(1-2)71-80.

Viswanathamurthi et al., Synthesis, characterization and biocidal studies of ruthenium (II) carbonyl complexes containing tetradentate Schiff bases. Transition Metal Chemistry. 1999; 24(6):638-641.

Volti et al., Carbon monoxide signaling in promoting angiogenesis in human microvessel endothelial cells. Antiox Redox Signal. May 2005;7(5-6):704-10.

Vreman et al., Determination of carbon monoxide (CO) in rodent tissue: effect of heme administration and environmental CO exposure. Anal Biochem. Jun. 15, 2005;341(2):280-9. Abstract only.

Waibel et al., Stable one-step technetium-99m labeling of His-tagged recombinant proteins with a novel Tc(I)-carbonyl complex. Nat Biotechnol. Sep. 1999;17(9):897-901.

Wang et al., Carbon monoxide-induced vasorelaxation and the underlying mechanisms. Br J Pharmacol. Jul. 1997;121(5):927-34.

Weigel et al., Inhibition of DNA replication in *Escherichia coli* by cyanide and carbon monoxide. J Biol Chem. Nov. 10, 1975;250(21):8536-42.

Wu et al., Carbon monoxide: endogenous production, physiological functions, and pharmacological applications. Pharmacol Rev. Dec. 2005;57(4):585-630. Review.

Xi et al., Carbon monoxide activates KCa channels in newborn arteriole smooth muscle cells by increasing apparent Ca2+ sensitivity of alpha-subunits. Am J Physiol Heart Circ Physiol. Feb. 2004;286(2):H610-8. Epub Oct. 16, 2003.

Xu et al., A facile method for synthesis of (R)-(−)- and (S)-(+)-homocitric acid lactones and related α-hydroxy dicarboxylic acids from d- or l-malic acid. Tetrahedron Lett. May 30, 2005;46(22):3815-18. Abstract only.

Yet et al., Induction of heme oxygenase-1 expression in vascular smooth muscle cells. A link to endotoxic shock. J Biol Chem. Feb. 14, 1997;272(7):4295-301.

Zhang et al., Carbon monoxide inhibition of apoptosis during ischemia-reperfusion lung injury is dependent on the p38 mitogen-activated protein kinase pathway and involves caspase 3. J Biol Chem. Jan. 10, 2003;278(2):1248-58. Epub Oct. 23, 2002.

Zimmerman et al., Cerebroprotective effects of the CO-releasing molecule CORM-A1 against seizure-induced neonatal vascular injury. Am J Physiol Heart Circ Physiol. Oct. 2007;293:H2501-H2507.

Zuckerbraun et al., Carbon monoxide protects against the development of experimental necrotizing enterocolitis. Am J Physiol Gastrointest Liver Physiol. Sep. 2005;289(3):G607-13. Epub May 12, 2005.

Zuckerbraun et al., Carbon monoxide reverses established pulmonary hypertension. J Exp Med. Sep. 4, 2006;203(9):2109-19. Epub Aug. 14, 2006.

Abe et al., The effects of prostacyclin analog OP-41483 on normothermic liver ischemia and reperfusion injury in rats. Prostaglandins Leukot Essent Fatty Acids. Jun. 1993;48(6):417-22.

Burleson et al., The effect of dyes used to evaluate the in situ, ex-vivo, and perfused kidney. Invest Urol. Nov. 1981;19(3):165-8. Abstract only. Accession No. PREV198273058212.

\* cited by examiner

Ru(CO)₃, Cl- Glycinate (CORM-3)

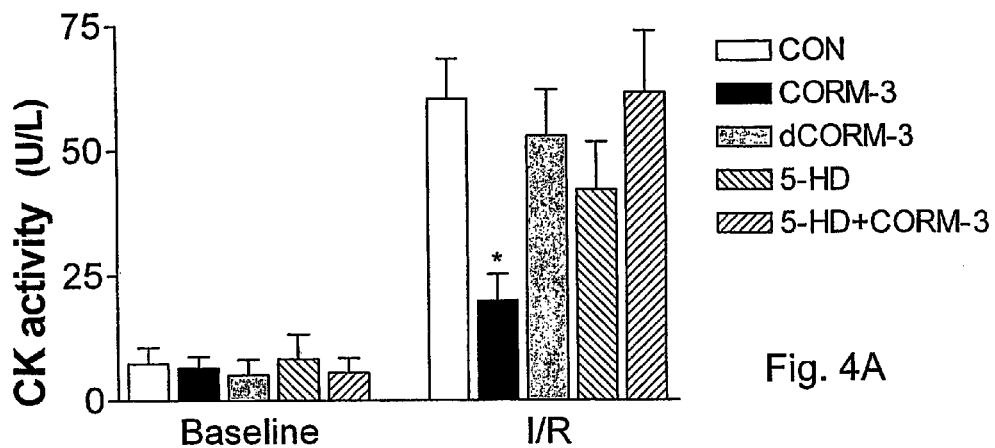
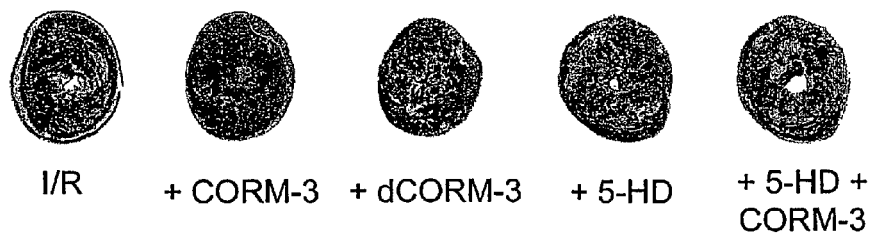
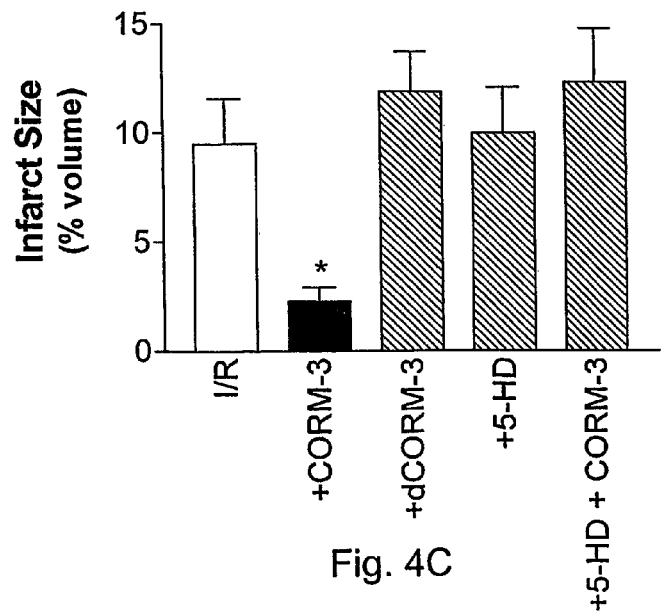
Fig. 4A
Fig. 4B
Fig. 4C

| Compound | Structure | MW | CO Release (20 µmoles) | | | | CO Release (40 µmoles) | | | | NOTES |
|---|---|---|---|---|---|---|---|---|---|---|---|
| | | | 0 | 10 | 20 | 30 | 0 | 10 | 20 | 30 | |
| CO-RM-1 | [Ru structure with CO and Cl ligands] | 512 | 12.0 ±3.0 | 16.3 ±4.0 | 18.1 ±4.3 | 18.5 ±4.8 | 28.5 ±0.4 | 32.0 ±0.2 | 34.5 ±0.5 | 35.6 ±0.4 | Soluble in DMSO |
| CO-RM-1a | [Ru structure with DMSO, Cl, CO ligands] | 384 | 7.2 ±0.6 | 8.6 ±0.3 | 8.0 ±0.4 | 7.5 ±0.4 | 16.9 ±0.6 | 18.4 ±0.3 | 17.3 ±0.3 | 16.7 ±0.2 | Soluble in DMSO |
| Negative control | [Ru structure with DMSO and Cl ligands] | 484 | N.D. | N.D. | N.D. | N.D. | N.D. | N.D. | N.D. | N.D. | Soluble in $H_2O$ |
| CO-RM-1b | [Ru structure with CO, Cl, DMSO ligands] | 334 | 6.4 ±1.2 | 7.3 ±0.6 | 8.2 ±0.1 | 8.7 ±0.3 | 11.7 ±0.8 | 13.7 ±0.9 | 14.0 ±1.1 | 14.4 ±0.6 | Soluble in DMSO |
| CO-RM-10 | $[Ru(CO)_2Cl_2]_n$ | (228) | 2.6 ±0.6 | 9.8 ±0.3 | 12.7 ±0.1 | 13.8 ±0.9 | 8.6 ±0.7 | 21.0 ±1.1 | 24.4 ±1.0 | 26.3 ±1.2 | Soluble in DMSO |

Fig. 5A

| | | | | | | | | | | |
|---|---|---|---|---|---|---|---|---|---|---|
| CO-RM-11 Ligand: THF | ![Ru(CO)3Cl2(THF)] | 328 | 5.6 ±0.6 | 5.9 ±0.6 | 6.2 ±1.1 | 6.2 ±1.2 | 10.9 ±0.2 | 12.3 ±0.4 | 13.3 ±0.4 | 13.7 ±0.2 | Soluble in DMSO |
| CO-RM-16 Ligand: Cytidine | ![Ru(CO)3Cl(Cyt)] | 742 | N.D. | 1.4 ±0.4 | 2.1 ±0.1 | 2.8 ±0.4 | 0.8 ±0.4 | 5.5 ±0.4 | 8.4 ±0.8 | 9.8 ±0.9 | Soluble in $H_2O$ |
| CO-RM-17 Ligand: Guanosine | ![Ru(CO)3Cl2(guan)] | 539 | 5.9 ±0.1 | 8.2 ±0.4 | 8.5 ±0.3 | 8.6 ±0.4 | 11.5 ±0.4 | 15.0 ±0.4 | 15.6 ±0.4 | 16.2 ±0.3 | Soluble in $H_2O$ |

Fig. 5B

| | | | | | | | | | | Soluble in H₂O |
|---|---|---|---|---|---|---|---|---|---|---|
| CO-RM-18 Ligand: Guanosine | [structure] 822 | 10.1 ±0.9 | 14.3 ±0.4 | 14.1 ±0.5 | 13.5 ±0.4 | 25.4 ±1.0 | 29.5 ±1.5 | 29.5 ±1.4 | 28.7 ±1.3 | Soluble in H₂O |
| CO-RM-22 Ligand: Guanine | [structure] 407 | 0.1 ±0.1 | 0.8 ±0.3 | 1.0 ±0.3 | 2.3 ±0.1 | 0.7 ±0.1 | 1.9 ±0.1 | 2.3 ±0.1 | 2.4 ±0.1 | Soluble in H₂O PPT |
| CO-RM-23 Ligand: Guanine | [structure] 558 | 1.2 ±0.1 | 1.3 ±0.2 | 1.3 ±0.1 | 1.0 ±0.2 | 2.7 ±0.3 | 2.7 ±0.3 | 2.7 ±0.4 | 2.3 ±0.2 | Soluble in H₂O PPT |
| CO-RM-26 Ligand: Cysteine | [structure] 340.5 | 0.6 ±0.1 | 1.9 ±0.1 | 2.3 ±0.2 | 2.4 ±0.2 | 1.9 ±0.2 | 3.7 ±0.1 | 5.1 ±0.1 | 5.2 ±0.1 | Soluble in H₂O |

Fig. 5C

| | | | | | | | | | |
|---|---|---|---|---|---|---|---|---|---|
| CO-RM-29 Ligand: Triacetyle-guanosine |  | 665 | 1.4 ±0.7 | 4.5 ±0.1 | 5.0 ±0.1 | 3.2 ±0.1 | 8.3 ±0.6 | 11.7 ±0.3 | 12.4 ±0.1 | 10.6 ±0.4 | Soluble in $H_2O$ |
| CO-RM-3 Ligand: Glycine |  | 294.5 | 14.2 ±0.6 | 17.8 ±0.7 | 14.3 ±0.7 | 12.9 ±0.7 | 25.2 ±1.5 | 24.4 ±1.0 | 23.8 ±0.6 | 23.2 ±0.3 | Soluble in $H_2O$ |
| CO-RM-38 Ligand: Isoleucine |  | 350.5 | 3.2 ±0.2 | 4.4 ±0.1 | 4.0 ±0.2 | 3.0 ±1.7 | 7.6 ±1.3 | 8.3 ±1.2 | 7.5 ±1.1 | 7.3 ±1.1 | Soluble in $H_2O$ |
| CO-RM-39 Ligand: Serine |  | 324.5 | 11.0 ±.03 | 12.8 ±.09 | 11.4 ±1.1 | 10.8 ±.07 | 24.2 ±1.5 | 24.6 ±1.4 | 22.0 ±1.0 | 21.9 ±1.2 | Soluble in $H_2O$ |
| CO-RM-40 Ligand: Alanine |  | 308.5 | 9.1 ±1.1 | 11.9 ±0.4 | 11.1 ±.03 | 11.0 ±0.2 | 20.2 ±.06 | 21.3 ±.09 | 19.9 ±.09 | 19.6 ±.09 | Soluble in $H_2O$ |

| | | | | | | | | | | |
|---|---|---|---|---|---|---|---|---|---|---|
| CO-RM-42 Ligand: Glutamine | (structure) | 365.5 | 8.9 ±0.4 | 11.1 ±0.4 | 12.1 ±1.4 | 10.1 ±0.3 | 21.4 ±2.1 | 21.8 ±2.2 | 20.6 ±2.0 | 20.0 ±1.8 | Soluble in H$_2$O |
| CO-RM-43 Ligand: Arginine | (structure) | 393.5 | 9.4 ±1.4 | 11.9 ±0.5 | 12.3 ±0.7 | 11.0 ±0.3 | 18.3 ±.03 | 20.0 ±0.6 | 19.0 ±1.2 | 17.8 ±1.3 | Soluble in H$_2$O |
| CO-RM-46 Ligand: Lysine | (structure) | 365.5 | 6.0 ±0.4 | 7.5 ±0.8 | 7.2 ±1.2 | 6.4 ±0.8 | 12.6 ±0.9 | 13.4 ±1.2 | 13.2 ±1.1 | 11.9 ±1.0 | Soluble in H$_2$O |
| CO-RM-67 Ligand: L-valine | (structure) | 336.5 | 11.1 ±2.9 | 18.2 ±1.7 | 17.6 ±1.6 | 17.0 ±1.6 | 29.3 ±1.5 | 34.6 ±2.2 | 33.7 ±2.2 | 32.8 ±2.2 | Soluble in H$_2$O |
| CO-RM-70 | (structure) | 240 | 0.5 ±0.2 | 0.9 ±0.1 | 2.2 ±0.2 | 2.7 ±0.3 | 0.9 ±0.1 | 2.0 ±0.2 | 4.9 ±0.2 | 6.3 ±0.3 | Soluble in DMSO PPT |
| CO-RM-71 | (structure) | 350 | 1.5 ±0.2 | 2.3 ±0.3 | 3.1 ±0.4 | 3.7 ±0.4 | 3.4 ±0.1 | 5.4 ±0.3 | 6.9 ±0.3 | 7.6 ±0.4 | Soluble in DMSO PPT |

Fig. 5E

| | | | | | | | | | |
|---|---|---|---|---|---|---|---|---|---|
| CO-RM-74<br>Ligand:<br>L-Threonine | [structure] | 338.5 | 15.7<br>±1.2 | 17.5<br>±2.0 | 16.5<br>±2.3 | 14.8<br>±2.2 | 33.3<br>±0.2 | 33.4<br>±0.1 | 32.7<br>±0.2 | 31.4<br>±0.1 | Soluble in<br>$H_2O$ |
| CO-RM-97 | [structure] | 316 | 2.8<br>±0.6 | 7.0<br>±0.7 | 7.2<br>±0.9 | 6.6<br>±0.9 | 7.1<br>±0.5 | 14.3<br>±0.7 | 14.7<br>±0.8 | 13.6<br>±0.7 | Soluble in<br>$H_2O$ |
| CO-RM-99 | [structure] | 317 | 4.6<br>±0.6 | 8.1<br>±0.2 | 7.3<br>±0.3 | 5.5<br>±0.3 | 11.5<br>±0.2 | 16.6<br>±0.2 | 16.0<br>±0.9 | 14.0<br>±0.2 | Soluble in<br>$H_2O$ |
| CO-RM-H<br>Ligand:<br>L-proline | [structure] | 335 | 1.4<br>±0.3 | 4.7<br>±0.6 | 6.2<br>±0.8 | 6.3<br>±0.7 | 4.2<br>±0.4 | 9.9<br>±0.2 | 12.5<br>±0.1 | 13.0<br>±0.1 | Soluble in<br>$H_2O$ |

Fig. 5F

THERAPEUTIC DELIVERY OF CARBON MONOXIDE TO EXTRACORPOREAL AND ISOLATED ORGANS

This application is the US national phase of international application PCT/GB2003/005050 filed 20 Nov. 2003, which designated the U.S. and claims priority of GB 0227138.5, filed 20 Nov. 2002, the entire contents of each of which are hereby incorporated by reference.

FIELD OF THE INVENTION

The present invention relates to methods of carbon monoxide delivery to extracorporeal and isolated organs of humans and other mammals.

BACKGROUND OF THE INVENTION

Transplant surgery is now used routinely in cases where patients have body organs that are damaged or malfunctioning. For example heart, lung, liver and kidney transplants are all well known. In transplant surgery, the patient's organ is removed and replaced with an organ donated by a donor. It is often necessary to transport a donated organ from the place of donation to the location of the transplant surgery. This can often involve transport of the donated organ over long distances. A donated organ in transit will be isolated from a blood supply and is therefore subject to ischaemic damage. It is important to limit this ischaemic damage, as any damage may affect the functioning of the organ after it has been transplanted.

It is also now common to perform surgery where an in situ body organ, tissue or part is isolated from the patient's blood supply. An example of this is heart valve replacement where the heart is stopped by a cardioplegic solution and the function of the heart is taken over by a mechanical pump system located outside of the body. In this case, the heart is isolated from the patient's blood supply. Again, there is a risk that an organ isolated in such a manner could be affected by ischaemic damage which is undesirable.

The beneficial physiological effects of carbon monoxide (CO) have been recognized and reported in a number of publications. A discussion of the background studies carried out in this area are reported in co-pending application WO 02/092075 published 21 Nov. 2002 which originates from work of the present inventors.

SUMMARY OF THE INVENTION

It can be seen that a method for limiting ischaemic damage of extracorporeal and isolated organs is required. The object of this invention is to provide such a method.

As exemplified by the experimental data detailed below, the present inventors have found that metal carbonyl compounds can be used to deliver CO to an extracorporeal or isolated organ so as to reduce ischaemic damage of the organ tissue.

Accordingly, in a first aspect, the present invention provides a method of treatment of an extracorporeal or isolated organ comprising contacting the organ with a composition including a metal carbonyl compound or pharmaceutically acceptable salt thereof and at least one pharmaceutically acceptable carrier. Typically the metal carbonyl makes available carbon monoxide (CO) to limit post-ischaemic damage.

Preferably, the metal carbonyl makes CO available by at least one of the following means:

1) CO derived by dissociation of the metal carbonyl is present in the composition in dissolved form;

2) on contact with a solvent or ligand the metal carbonyl releases CO;

3) on contact with a tissue, organ or cell the metal carbonyl releases CO; 4) on irradiation, the metal carbonyl releases CO.

While the invention is primarily here discussed as involving the delivery of carbon monoxide to the organ being treated wherein the metal carbonyl makes CO available for physiological effect, it is not excluded that a different mechanism is involved, such as that the metal carbonyl acts directly without release of CO.

The organ treated in the method of the invention is an organ which is isolated from the blood supply. The organ may be extracorporeal e.g. a donated organ outside of the donor's body, or it may be isolated in the sense that it is in a patient's body and isolated from the blood supply for surgical purposes.

The organ may be, for example, a circulatory organ, respiratory organ, urinary organ, digestive organ, reproductive organ, neurological organ, muscle or skin flap or an artificial organ containing viable cells. Most preferably, the organ is a heart, lung, kidney or liver. The contacting with the compositions containing metal carbonyl can be achieved by any method that exposes the organ to the composition e.g. bathing or pumping. Preferably, an isolated organ which is attached to the body, i.e. a bypassed organ, is perfused with the composition. An organ which is extracorporeal is preferably bathed in the composition.

The term "compound" includes species generated on dissolution.

Certain metal carbonyl compounds are capable of releasing CO on contact with a suitable solvent. The solvent may form a component part of the composition. Thus in this aspect of the invention, the treatment uses CO derived from the metal carbonyl in dissolved form. The conditions under which the carbonyl compound is dissolved in the solvent during preparation of the composition may be controlled such that the CO thus released is retained in solution. This may be facilitated where an equilibrium exists between the dissociated components and the undissociated carbonyl.

The dissociated components of the parent carbonyl may themselves be metal carbonyl complexes capable of releasing further CO. For example, when $[Ru(CO)_3Cl_2]_2$ is dissolved in DMSO, CO is liberated into solution, and a mixture of tri-carbonyl and di-carbonyl complexes is formed, and these themselves may be capable of releasing further CO.

Release of CO from the complex can be stimulated by reaction with a ligand in solution which for example replaces one of the ligands of the complex leading to loss of CO from the complex. The ligand may be one containing sulphur or nitrogen. Some metal carbonyls may release CO on contact with biological ligands such as glutathione or histidine.

In a further aspect of the invention, the composition may not itself contain dissolved CO, but may be prepared such as to release CO on contact with a suitable solvent or medium. For example, the composition may contain a metal carbonyl compound capable of releasing CO on contact with, for example, water, cardioplegic fluids or perfluorocarbon type blood substitutes.

Alternatively, the composition may be intended to be dissolved in water prior to administration. Such compositions may be prepared in solution or in solid form, such as in tablet form. If they are in solution form, they will typically be prepared in a solvent which does not support dissociation of the metal carbonyl compound, such that release of CO takes place only on contact with the appropriate substance.

In another aspect of the invention the composition may contain a metal carbonyl compound which releases CO on contact with a tissue, organ or cell. It is known that certain metal carbonyl compounds do not release CO to solution but are nevertheless capable of releasing CO to physiological cellular materials or tissues, such as vascular endothelium. For example, $[Fe(SPh)_2(2,2'-bipyridine)(CO)_2]$ is known not to release CO to myoglobin in solution, but is nevertheless capable of promoting dilatation of pre-contracted aortic rings. Without wishing to be limited by any particular theory, it is thought that CO may be released from such compounds as a result of an oxidation-reduction reaction, mediated by cellular components such as cytochromes.

However the invention is not limited to a redox reaction as a mechanism for CO release, since loss of at least a first CO from the complex may occur without redox.

As yet another alternative, the metal carbonyl compound may release CO on irradiation. The compound may be irradiated prior to administration, for example to produce a solution of dissolved CO, or may be irradiated in situ after administration. It is contemplated that such compositions may be used to provide controlled, localised release of CO. For example, a pharmaceutical composition of this type may be administered and CO released specifically at a site in need thereof, e.g. to induce vasodilation, by localised irradiation by means of a laser or other radiant energy source, such as UV rays.

Typically the compositions of the present invention release CO such as to make it available to the isolated organ in dissolved form. However, in some circumstances CO may be released from a metal carbonyl directly to a non-solvent acceptor molecule.

It will be apparent that compositions according to the present invention may be capable of delivering CO through one or more of the above described modes of action.

Typically the metal carbonyl compound comprises a complex of a transition metal, preferably a transition metal from groups 6 to 10 (in this specification the groups of the periodic table are numbered according to the IUPAC system from 1 to 18). The number of carbonyl ligands is not limited, provided at least one carbonyl ligand is present. The preferred metals are transition metals of lower molecular weight, in particular Fe, Ru, Mn, Co, Ni, Mo and Rh. Two other metals which may be used are Pd and Pt. In the metal carbonyl complexes used in the invention, the metal is typically in a low oxidation state, i.e. O, I or II. For the metals preferred, the oxidation states are typically not higher than $Fe^{II}$, $Ru^{II}$, $Mn^I$, $Co^{II}$ or $Co^{II}$ preferably $Co^I$, $Rh^{III}$ preferably $Rh^I$, $Ni^{II}$, $Mo^{II}$. The metal is preferably not a radionuclide. Fe is one particularly suitable metal, since Fe is present in quantity in mammals.

The metal carbonyl compounds may be regarded as complexes, because they comprise CO groups coordinated to a metal centre. However the metal may be bonded to other groups by other than coordination bonds, e.g. by ionic or covalent bonds. Thus groups other than CO which form part of the metal carbonyl compound need not strictly be "ligands" in the sense of being coordinated to a metal centre via a lone electron pair, but will be referred to herein as "ligands" for ease of reference.

The carbonyl compound preferably comprises at least one modulatory ligand. By this is meant a ligand which is not CO, but which modulates a particular property of the complex, such as the tendency to release CO, solubility, hydrophobicity, stability, electrochemical potential, etc. Thus suitable choices of ligand may be made in order to modulate the behaviour of the compound. For example it may be desirable to modulate the solubility of the compound in organic and/or aqueous solvents, its ability to cross cell membranes, its rate of release of CO on contact with a particular solvent or cell type, etc.

Such ligands are typically neutral or anionic ligands, such as halide, or derived from Lewis bases and having N, P, O, S or C as the coordinating atom(s). Preferred coordinating atoms are N, O and S. Examples include, but are not limited to, sulfoxides such as dimethylsulfoxide, natural and synthetic amino acids and their salts for example, glycine, cysteine, and proline, amines such as $NEt_3$ and $H_2NCH_2CH_2NH_2$, aromatic bases and their analogues, for example, bi-2,2'-pyridyl, indole, pyrimidine and cytidine, pyrroles such as biliverdin and bilirubin, drug molecules such as YC-1 (2-(5'-hydroxymethyl-2'-furyl)-1-benzylindazole), thiols and thiolates such as EtSH and PhSH, chloride, bromide and iodide, carboxylates such as formate, acetate, and oxalate, ethers such as $Et_2O$ and tetrahydrofuran, alcohols such as EtOH, and nitriles such as MeCN. Particularly preferred are coordinating ligands, such as amino acids, which render the carbonyl complex stable in aqueous solution. Other possible ligands are conjugated carbon groups, such as dienes. One class of ligands which can provide metal carbonyl compounds of use in this invention is cyclopentadienyl ($C_5H_5$) and substituted cyclopentadienyl. The substituent group in substituted cyclopentadienyl may be for example an alkanol, an ether or an ester, e.g. $-(CH_2)_nOH$ where n is 1 to 4, particularly $-CH_2OH$, $-(CH_2)_nOR$ where n is 1 to 4 and R is hydrocarbon preferably alkyl of 1 to 4 carbon atoms and $-(CH_2)_nOOCR$ where n is 1 to 4 and R is hydrocarbon preferably alkyl of 1 to 4 carbon atoms. The preferred metal in such a cyclopentadienyl or substituted cyclopentadienyl carbonyl complex is Fe. Preferably the cyclopentadienyl carbonyl complex is cationic, being associated with an anion such as chloride.

CO is suggested to act at least in part through the stimulation of guanylate cyclase activity. Thus the metal carbonyl compound may desirably comprise ligands which modulate the effect of CO on guanylate cyclase. For example, the drug YC-1 (3-(5'-hydroxymethyl-2'-furyl)-1-benzylindole) is thought to enhance stimulation of guanylate cyclase by CO. Thus incorporation of ligands such as YC-1 or derivatives thereof into the metal carbonyl compounds can alter or enhance the biological effects of the released CO.

The metal carbonyl compound may further comprise a targeting moiety, to facilitate release of CO at an appropriate site. The targeting moiety is typically capable of binding a receptor on a particular target cell surface, in order to promote release of CO at the required site. The targeting moiety may be a part of a modulating ligand capable of binding to a receptor found on the surface of the target cells, or may be derived from another molecule, such as an antibody directed against a particular receptor, joined to the complex by a suitable linker.

In most preferred embodiments, the treatment uses a composition for delivery of CO, comprising as active ingredient a compound of the formula $M(CO)_xA_y$ where x is at least one, y is at least one, M is a metal, A is an atom or group bonded to M by an ionic, covalent or coordination bond but is not CO, and, in the case where y>1, each A may be the same or different, or a pharmaceutically acceptable salt of such a compound. Typically, M is a transition metal, particularly of groups 6 to 10, and A may be selected from neutral or anionic ligands such as halide or derived from Lewis bases and having N, P, O, S or C as the coordinating atom. Mono-, bi- or poly-dentate ligands may be used. More details of preferred metals and ligands are given above. The molecular weight of the compound is preferably less than 1000, e.g. not more than 822. Some useful CO-releasing metal carbonyls are given in FIGS. 5A to 5F.

The carbonyl complex should be pharmaceutically acceptable, in particular non-toxic or of acceptable toxicity at the dosage levels envisaged.

Most preferably, the treatment uses a metal carbonyl compound of the formula $$M(CO)_xA_yB_z \text{ where}$$

M is Fe, Co or Ru,
x is at least one,
y is at least one,
z is zero or at least one,
each A is a ligand other than CO and is monodentate or polydentate with respect to M and is selected from the amino acids
  alanine
  arginine
  asparagine
  aspartic acid
  cysteine
  glutamic acid
  glutamine
  glycine
  histidine
  isoleucine
  leucine
  lysine
  methionine
  phenylalanine
  proline
  serine
  threonine
  tryptophan
  tyrosine
  valine
  $[O(CH_2COO)_2]^{2-}$ and
  $[NH(CH_2COO)_2]^{2-}$, and
B is optional and is a ligand other than CO
x is preferably 3, y is preferably 1 and z is preferably 1.

The term amino acid here used includes the species obtained by loss of the acidic hydrogen, such as glycinato.

$B_z$ represents one or more optional other ligands. There are no particular limitations on B and ligands such as halides, e.g. chloride, bromide, iodide, and carboxylates, e.g. acetate may be used.

M is selected from Fe, Ru and Co. These metals are preferably in low oxidation states, as described above.

The compositions used the present invention typically comprise a pharmaceutically acceptable excipient, carrier, buffer, stabiliser or other materials well known to those skilled in the art. Such materials should be non-toxic and should not interfere unduly with the efficacy of the active ingredient. Examples include St Thomas Hospital solutions, Euro-Collins solutions, University of Wisconsin solutions, Celsior solutions, Ringer Lactate solutions, Bretschneider solutions and perflurorcarbons. More information can be found in Nydegger et al, Transplant Immunology, 9 (2002) p 215-225.

The compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Pharmaceutically acceptable amounts of other solvents may also be included, in particular where they are required for dissolving the particular metal carbonyl compound contained in the composition. The composition may further comprise pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); preservatives (e.g. methyl or propyl-p-hydroxybenzoates or sorbic acid); and energy sources (e.g. carbohydrates such as glucose, fats such as palmitate or amino acid).

The temperature at which the treatment is carried out is preferably between 15 and 37° C. for organs still attached to the body but isolated form the blood supply and between 2 and 10° C. for extracorporeal organs, preferably 4° C.

The amount of CO delivered in the treatment is preferably a prophylactically effective amount. The actual amount administered, and rate and time-course of administration, will depend on the nature of the organ.

The present invention also provides the use of a metal carbonyl compound as herein described in the manufacture of a medicament for treatment of an extracorporeal or isolated organ to reduce ischaemic damage of the organ whilst it is isolated from a blood supply.

Throughout this application, references to medical treatment are intended to include both human and veterinary treatment, and references to pharmaceutical compositions are accordingly intended to encompass compositions for use in human or veterinary treatment.

INTRODUCTION OF THE DRAWINGS

Experimental data illustrating the present invention will now be described by reference to the accompanying figures, in which.

FIGS. 2A, 2B, 2C, 3A, and 3B show the effects of various treatments on isolated, perfused rat hearts;

FIGS. 4A, B and C show the extent of tissue injury; and

FIGS. 5A to F show metal carbonyl compounds.

EMBODIMENTS OF THE INVENTION AND EXPERIMENTAL DATA

Reagents and Material

Tricarbonyldichloro ruthenium(II) dimer ($[Ru(CO)_3Cl_2]_2$), 5-hydroxynoneate (5-HD), 2,3,5-triphenyltetrazolium chloride (tetrazolium red) and all the other reagents were purchased from Sigma (Poole, Dorset) unless specified otherwise.

Stock solutions of $Ru(CO)_3Cl(NH_2CH_2CO_2)$(CORM-3) (8 mM) were prepared by solubilizing the compound in distilled water. Synthesis of CORM-3 are described below. Decomposed CORM-3 (dCORM-3) was prepared by dissolving CORM-3 in Krebs-Henseleit buffer and allowing the solution to stand overnight (18 h) at room temperature. 2,3,5-triphenyl-tetrazolium chloride (tetrazolium red) solution (3% w/v) was prepared freshly in Krebs-Henseleit buffer at the end of each experimental protocol prior to infusion into the isolated heart.

All data are expressed as mean±s.e.m. Differences between the groups analysed were assessed by the Student's two-tailed t-test, and an analysis of variance (ANOVA) was performed where more than two treatments were compared. Results were considered statistically significant at P<0.05.

Herein, "mM" and "µM" signify concentrations (millimolar and micromolar respectively).

Detection of CO Release

The release of CO from CORM-3 or dCOMR-3 was assessed spectrophotometrically by measuring the conversion of deoxymyoglobin (deoxy-Mb) to carbonmonoxy myoglobin (MbCO) as previously described [3]. The amount of MbCO formed was quantified by measuring the absorbance at 540 nm (extinction coefficient=15.4 $M^{-1}$ $cm^{-1}$). Myoglobin solutions (66 µmol/L final concentration) were prepared fresh by dissolving the protein in 0.04 M phosphate buffer (pH 6.8). Sodium dithionite (0.1%) was added to convert myoglobin to deoxy-Mb prior to each reading.

Figure 1A:
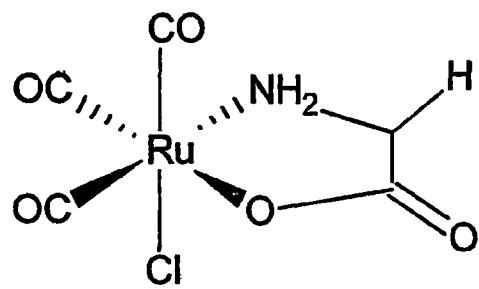
FIG. 1A shows the structure of tricarbonylchloro-(glycinato)ruthenium(II) (CORM-3)
Figure 1B:
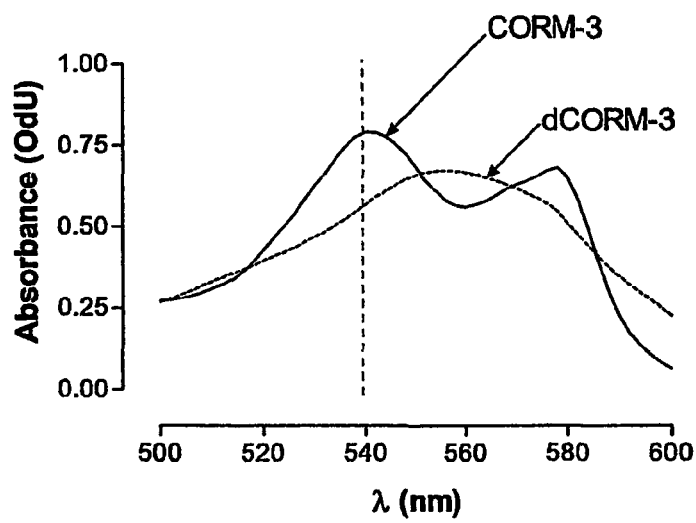
FIG. 1B shows the deoxy-myoglobin and CO-myoglobin absorption spectra.
Figure 1C:
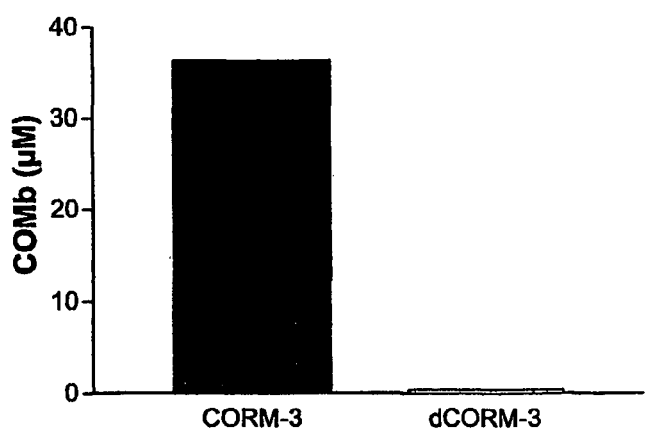
FIG. 1C shows conversion to MbCO.

When CORM-3 was prepared in distilled water and then added to the phosphate buffer solution containing Mb, a spectrum characteristic of MbCO was rapidly detected (FIG. 1B). The amount of MbCO measured after the reaction revealed that 1 mole of CO was liberated per mole of CORM-3. In fact, as shown in FIG. 1C, addition of 40 µM CORM-3 resulted in the formation of 36.4±0.9 µM MbCO. When dissolved in water and left for 24 h at room temperature, CORM-3 retained its full ability to liberate CO as assessed by the conversion of Mb to MbCO (data not shown). In contrast, it was discovered that CORM-3 prepared in Krebs-Henseleit buffer gradually decomposed over time and lost its ability to release CO. As shown in FIGS. 1B and 1C, CORM-3 in Krebs-Henseleit buffer left overnight at room temperature (dCORM-3) failed to convert deoxy-Mb to MbCO. These data reveal that CORM-3 prepared in water is relatively stable and that physiological solutions such as Krebs-Henseleit and phosphate buffers favour the release of CO from this metal carbonyl complex.

Isolated Heart Preparation

Isolated hearts from male Lewis rats (300-350 g) were perfused according to the Langendorff technique as previously described by our group [4]. Briefly, hearts were rapidly excised and perfused at constant flow (11 ml/min) with Krebs-Henseleit buffer (in mM: 119 NaCl, 4.7 KCl, 2.5 $CaCl_2$, 1.66 $MgSO_4$, 24.9 $NaHCO_3$, 1.18 $KH_2PO_4$, 5.55 glucose, 2.00 sodium pyruvate, 0.5 EGTA) bubbled with 95% $O_2$ and 5% $CO_2$ at 37° C. (pH 7.4). Coronary perfusion pressure (CPP) was continuously measured by a pressure transducer (Grass Instruments, Astromed, RI, USA) connected to the aortic cannula. A latex balloon filled with saline was inserted into the left ventricle through the atrium and connected by a catheter to a second pressure transducer. The balloon was inflated to provide an initial end-diastolic pressure (EDP) of 10 mmHg. Both transducers were connected to a computer and data were acquired with BioPac™ instrumentation and analyzed with the accompanying AcqKnowledge™ software (BIOPAC System Inc.). Left ventricular developed pressure (LVDP), heart rate (HR), maximal contraction (+dP/dt) and relaxation (−dP/dt) rates, CPP and EDP were continuously recorded throughout the period of perfusion.

Ischaemia-Reperfusion Model

Isolated hearts were allowed to equilibrate at constant flow for 30 min and then made globally ischaemic by interrupting the buffer perfusion. Ischaemic hearts were kept at 37° C. in the water-jacketed chamber for 30 min and then reperfused for 60 min. All the hemodynamic parameters were continuously monitored throughout the experimental protocol as reported above. Krebs buffer was collected for 10 min from the pulmonary artery prior to the ischaemic event and in the last 10 min of reperfusion for creatine kinase (CK) analysis. At the end of reperfusion, hearts were stained to assess tissue viability using tetrazolium red. In additional experiments, hearts made ischaemic were infused for the first 10 min of reperfusion with CORM-3 or dCORM-3 (10 µM final concentration) via a syringe pump connected to the side arm of the aortic cannula. To assess a possible role of mitochondrial ATP-dependent potassium channels ($K_{ATP}$) in cardioprotection mediated by CORM-3, control hearts or hearts receiving CORM-3 were pre-treated for 10 min prior to ischaemia with 5-hydroxydodecanoate (5-HD, 50 µM final concentration), a specific blocker of mitochondrial $K_{ATP}$.

Determination of Infarct Size and Cardiac Muscle Damage

Hearts from each experimental group (n=5) were stained for tissue viability at the end of the reperfusion period. Hearts were perfused through a side arm of the aortic cannula for 20 min with tetrazolium red (3% w/v) in Krebs Henseleit buffer at 37° C. The tetrazolium salt stains the viable myocardium brick red, whereas the infarcted tissue remains unstained and appears white. After staining, hearts were removed and stored in 2% formalin in the dark prior to analysis. Hearts were carefully cut into 2-mm thick sections, scanned into a computer using an AGFA Arcus® II scanner and the total ischaemic size was determined by volumetric analysis software (Scion Image®, Scion Corporation, MA, USA). Cardiac muscle damage was assessed by measuring the release of creatine kinase (CK) into the perfusate using a commercially available spectrophotometric assay kit (DG147-A) from Sigma Diagnostic (Poole, Dorset).

Results

Figure 2A:
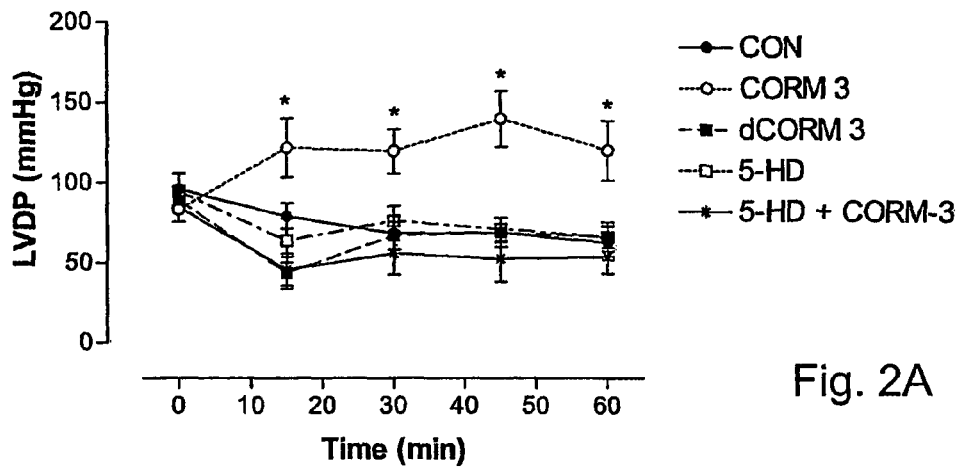
Figure 2B:
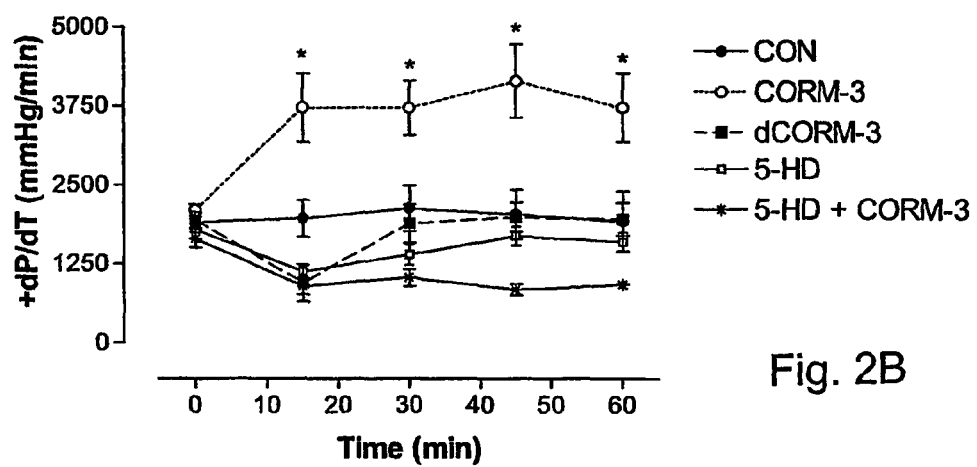
Figure 2C:
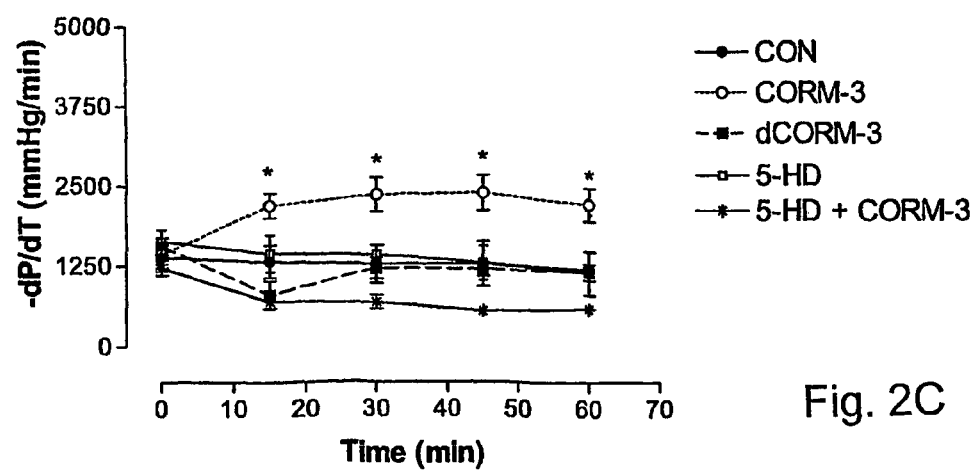
Figure 3A:
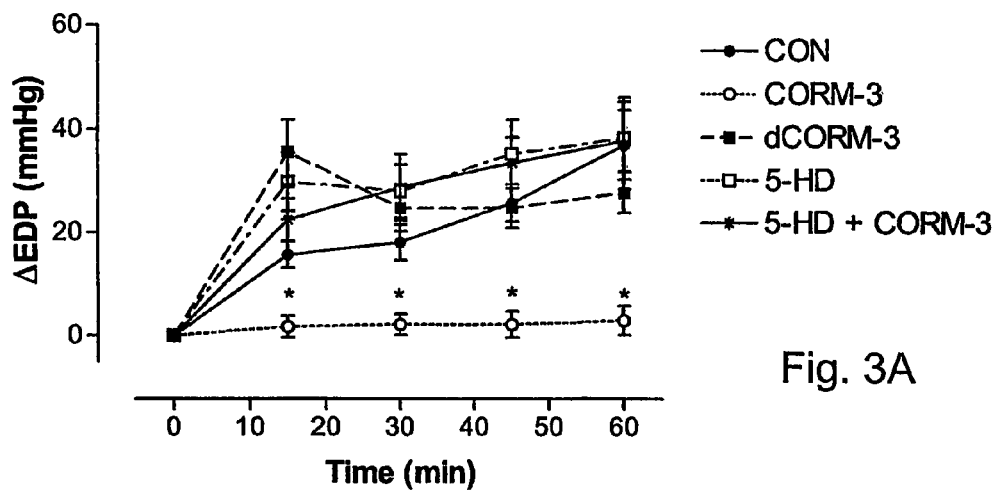
Figure 3B:
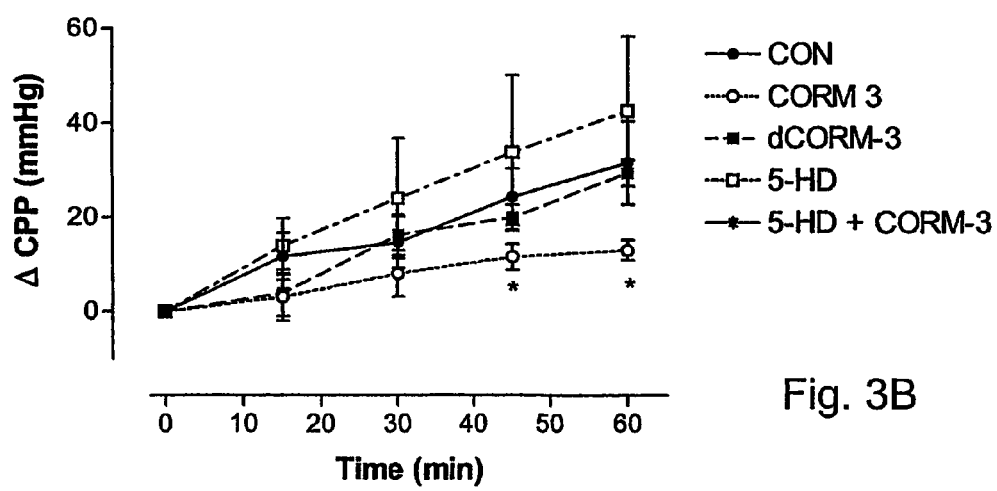
Figure 5D:
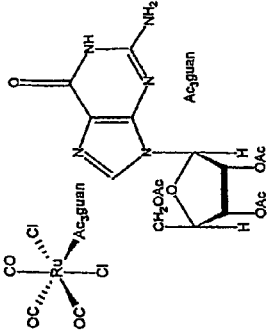
Figure 5D:
Figure 5D:
Figure 5D:
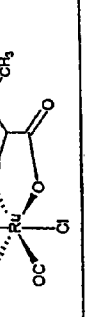
Figure 5D:
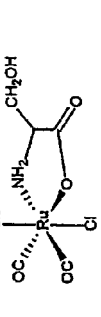

Hemodynamic, biochemical and histological parameters were measured to assess the potential beneficial effects of CORM-3 on the functional recovery of hearts subjected to ischaemia-reperfusion. As shown in FIGS. 2A, 2B and 2C, the cardiac performance of hearts treated with CORM-3 at reperfusion was significantly higher compared to control hearts (data marked 'CON' in Figures). After 60 min of reperfusion, control hearts displayed a 34% decrease in left ventricular-developed pressure (LVDP) compared to baseline whereas hearts reperfused in the presence of CORM-3 showed a 44% increase in this parameter (p<0.05, FIG. 2A). This positive inotropic effect mediated by CORM-3 was also evident when analyzing the maximal rate of contraction (+dP/dt) and relaxation (−dP/dt) in post-ischaemic hearts (see FIGS. 2B and 2C). While no significant changes in +dP/dt and −dP/dt were observed in control hearts after ischaemia-reperfusion, hearts reperfused in the presence of CORM-3 showed a significant increase in both +dP/dt (from 2099±99 to 3726±542 mmHg/s, p<0.05) and −dP/dt (from 1432±149 to 2207±258 mmHg/s, p<0.05). CORM-3 was also capable of preventing the increases in end diastolic (EDP) and coronary perfusion pressure (CPP) that are typical of post-ischaemic myocardial dysfunction in this model. As shown in FIGS. 3A and 3B, control hearts showed an increase of 36.9±8.4 mmHg in EDP and 31.6±8.8 mmHg in CPP at the end of reperfusion whereas CORM-3 significantly attenuated these effects (3±1.8 and 13±2.2 mmHg for EDP and CPP, respectively; p<0.05). Biochemical and histological analysis confirmed the beneficial effect of CORM-3 in ameliorating the functional recovery of the ischaemic hearts. Creatine kinase (CK) activity, an index of cardiac tissue injury, was elevated in the buffer of reperfused control hearts (from 7.4±3.2 to 60.4±8.0 U/L) but the activity was significantly attenuated in the presence of CORM-3 (from 6.5±2.3 to 19.9±5.3 U/L) (p<0.05, see FIG. 4A). Similarly, the infarct size measured by staining the myocardial tissue with tetrazolium red at the end of the reperfusion period was significantly (p<0.05) reduced in hearts reperfused with CORM-3 (2.3±0.6%) compared to control (9.5±2.1%) (FIGS. 4B and 4C). It is interesting to note that the cardioprotective action elicited by CORM-3 as observed from all the parameters measured can be attributed to CO being liberated from this metal carbonyl during the reperfusion period. In fact, the negative control dCORM-3, which is incapable of releasing CO (see FIGS. 1B and 1C), did not promote any protective effect on the hemodynamic, biochemical and histological parameters measured (see FIGS. 2-4).

Mechanism of Cardioprotection by CORM-3: Possible Involvement of K Channels

The potassium ion ($K^+$) is the major cytoplasmic and mitochondrial cation, and net flux of $K^+$ across the inner membrane critically regulates mitochondrial activity including regulation of energy production (ATP) and maintenance of calcium homeostasis, which are both essential for cellular survival [1]. The ATP-sensitive $K^+$ channel ($K_{ATP}$) has been identified as an important regulator of $K^+$ flux and the opening of this channel has been implicated in protection of the myocardium against ischaemia-reperfusion [1, 2, 5]. Blockade of $K_{ATP}$ channels with specific inhibitors such as 5-hydroxydodecanoate (5-HD) has been shown to exacerbate myocardial dysfunction and tissue damage during ischaemia reperfusion [5]. CO has also been shown to activate the opening of a different type of $K^+$ channel that regulate the flux of calcium ($K_{ca}$) in smooth muscle cells and mediates vaso-relaxation [6, 7]. Therefore, it was hypothesized that part of the cardioprotective mechanism mediated by CORM-3 could involve the activation of $K_{ATP}$ mitochondrial channels. The data presented in FIGS. 2, 3 and 4 corroborate this hypothesis. In fact, the protective effects of CORM-3 in preserving myocardial contractility (LVDP, +dP/dt and –dP/dt) and preventing the increases in diastolic and coronary pressures (EDP and CPP) during reperfusion following the ischaemic event are totally abolished by pre-treatment of isolated hearts with 5-HD, an inhibitor of $K_{ATP}$ mitochondrial channel (FIGS. 2 and 3, respectively). Moreover, the levels of CK in the buffer at the end of reperfusion and the extent of the infarct size in hearts treated with 5-HD and CORM-3 were similar to control hearts and significantly higher (p<0.05) compared to hearts treated with CORM-3 alone (FIG. 4). The data indicate that CO released by CORM-3 could facilitate the opening of $K_{ATP}$ channels which are crucial for maintaining cardiac function following ischaemic episodes.

Syntheses

Synthetic methods for obtaining compounds shown in FIGS. 5A to 5F are disclosed in WO 02/092075, the entire content of which is incorporated herein by reference. These Co-releasing compounds are examples of those useful in the present invention. The CO release data in FIGS. 5A to 5F is explained in WO 02/092075.

By way of example, the synthesis of CORM-3 Ru(CO)$_3$Cl (NH$_2$CH$_2$CO$_2$) is set out below. Purity of the product has not been investigated in detail.

Preparation of Ru(CO)$_3$Cl(NH$_2$CH$_2$CO$_2$) [M$_R$ 294.5] Glycine Complex. Reference Number: CORM-3

[Ru(CO)$_3$Cl$_2$]$_2$ (0.129 g, 0.25 mmol) and glycine (0.039 g, 0.5 mmol) were placed under nitrogen in a round bottomed flask. Methanol (75 cm$^3$) and sodium ethoxide (0.034 g, 0.50 mmol) were added and the reaction allowed to stir for 18 hours at room temperature. The solvent was then removed under pressure and the yellow residue redissolved in THF, filtered and excess 40-60 light petroleum added. The yellow solution was evaporated down to give a pale yellow solid (0.142 g, 96%). The product was stored in closed vials at 4° C.

Alternative, Preferred Preparation of Ru(CO)$_3$Cl (NH$_2$CH$_2$CO$_2$) [M$_R$ 294.6] Glycine Complex. Reference Number: CORM-3.

[Ru(CO)$_3$Cl$_2$]$_2$ (0.129 g, 0.25 mmol) and glycine (0.039 g, 0.50 mmol) were placed under nitrogen in a round bottomed flask. Methanol (40 cm$^3$) and sodium methoxide (0.5M solution in MeOH, 1.00 cm$^3$, 0.50 mmol) were added and the reaction stirred for 18 hours. HCl (2.0 M solution in diethyl ether) was added in small aliquots until the IR band at 1987 cm$^{-1}$ in solution IR spectroscopy could no longer be detected. The solvent was then removed under reduced pressure and the yellow residue redissolved in THF, filtered and an excess of 40-60 light petroleum added. The resulting precipitate was isolated by pipetting off the mother liquor and drying under high vaccum. The same work up was repeated for the mother liquor once concentrated. The colour of the product varied between whit and pale yellow and was produced in an average yield of 0.133 g, (90%).

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

REFERENCES

1. Holmuhamedov E L, Jovanovic S, Dzeja P P, Jovanovic A and Terzic A. Mitochondrial ATP-sensitive $K^+$ channels modulate cardiac mitochondrial function. *Am J Physiol* 275: H1567-H1576, 1998.
2. Lawton J S, Hsia P W, McClain L C, Maier G W and Damiano R J, Jr. Myocardial oxygen consumption in the rabbit heart after ischemia: hyperpolarized arrest with pinacidil versus depolarized hyperkalemic arrest. *Circulation* 96: II-52, 1997.
3. Motterlini R, Clark J E, Foresti R, Sarathchandra P, Mann B E and Green C J. Carbon monoxide-releasing molecules: characterization of biochemical and vascular activities. *Circ Res* 90: E17-E24, 2002.
4. Motterlini R, Samaja M, Tarantola M, Micheletti R and Bianchi G. Functional and metabolic effects of propionyl-L-carnitine in the isolated perfused hypertrophied rat heart. *Mol Cell Biochem* 116: 139-145, 1992.
5. Wang L, Cherednichenko G, Hernandez L, Halow J, Camacho S A, Figueredo V and Schaefer S. Preconditioning limits mitochondrial Ca$^{2+}$ during ischemia in rat hearts: role of $K_{ATP}$ (channels). *Am J Physiol Heart Circ Physiol* 280: H2321-H2328, 2001.
6. Wang R and Wu L. The chemical modification of $K_{ca}$ channels by carbon monoxide in vascular smooth muscle cells. *J Biol Chem* 272: 8222-8226, 1997.
7. Wu L, Cao K, Lu Y and Wang R. Different mechanisms underlying the stimulation of K(Ca) channels by nitric oxide and carbon monoxide. *J Clin Invest* 110: 691-700, 2002.

The invention claimed is:

1. A method of treatment of an extracorporeal organ that is a donated transplantation organ and is outside the donor's body or an isolated organ of a patient that is inside or attached to a patient's body but is isolated from the patient's blood supply, said method comprising contacting the extracorporeal organ of a donor or the isolated organ of a patient with a composition including a carbon monoxide-releasing metal carbonyl compound or pharmaceutically acceptable salt thereof and at least one pharmaceutically acceptable carrier to limit post-ischemic damage to said extracorporeal organ of a donor or said isolated organ of a patient;

wherein the carbon monoxide-releasing metal carbonyl compound is of the formula $M(CO)_xA_yB_z$, where x is at least one, y is at least one, M is a transition metal;

each A is a ligand other than CO and is monodentate or polydentate with respect to M and is selected from:
alanine,
arginine,
asparagine,
aspartic acid,
cysteine,
glutamic acid,
glutamine,
glycine,
histidine,
isoleucine,
leucine,
lysine,
methionine,
phenylalanine,
proline,
serine,
threonine,
tryptophan,
tyrosine,
valine,
$[O(CH_2COO)_2]^{2-}$, and
$[NH(CH_2COO)_2]^{2-}$, and
B is optional and is a ligand other than CO.

2. A method according to claim 1, wherein said metal carbonyl compound makes CO available by at least one of the following means:
CO derived by dissociation of the metal carbonyl compound is present in the composition in dissolved form;
on contact with a solvent the metal carbonyl compound releases CO;
on contact with a tissue, organ or cell, the metal carbonyl compound releases CO;
on irradiation, the metal carbonyl compound releases CO.

3. A method according to claim 1, wherein treatment is of said extracorporeal organ of a donor.

4. A method according to claim 1, wherein treatment is of said isolated organ of a patient.

5. A method according to claim 1, wherein the contacting step includes perfusing said organ with said composition.

6. A method according to claim 1, wherein:
M is Fe, Co, Mn, Mo, or Ru.

7. The method of claim 1, wherein the extracorporeal organ of a donor is treated at a temperature in the range of 2 to 10° C.

8. A method according to claim 7, wherein said metal carbonyl compound makes CO available by at least one of the following means:
CO derived by dissociation of the metal carbonyl compound is present in the composition in dissolved form;
on contact with a solvent, the metal carbonyl compound releases CO;
on contact with a tissue, organ, or cell, the metal carbonyl compound releases CO;
on irradiation, the metal carbonyl compound releases CO.

9. A method according to claim 7, wherein the contacting step includes perfusing said organ with said composition.

10. The method of claim 7, wherein M is Fe, Co, Mn, Mo, or Ru.

11. The method of claim 6 or 7, wherein M is Fe.

12. The method of claim 6 or 7, wherein M is Ru.

13. The method of claim 6 or 7, wherein M is Mo.

* * * * *

UNITED STATES PATENT AND TRADEMARK OFFICE
CERTIFICATE OF CORRECTION

| | |
|---|---|
| PATENT NO. | : 7,989,650 B2 |
| APPLICATION NO. | : 10/535508 |
| DATED | : August 2, 2011 |
| INVENTOR(S) | : Roberto Angelo Motterlini et al. |

It is certified that error appears in the above-identified patent and that said Letters Patent is hereby corrected as shown below:

At column 12, claim 2, line 3, please change "organ or cell" to --organ, or cell--

At column 12, claim 7, line 14, please change "The method" to --A method--

Signed and Sealed this
Twenty-fifth Day of October, 2011

David J. Kappos
*Director of the United States Patent and Trademark Office*